(12) United States Patent
Markland et al.

(10) Patent No.: US 9,216,152 B2
(45) Date of Patent: Dec. 22, 2015

(54) INJECTABLE DELIVERY OF MICROPARTICLES AND COMPOSITIONS THEREFORE

(75) Inventors: Peter Markland, Birmingham, AL (US); Gary Anthony Winchester, Dora, AL (US); Thomas Robert Tice, Indian Springs, AL (US); David P. Martin, Arlington, MA (US)

(73) Assignees: Tepha, Inc., Lexington, MA (US); Evonik Corporation, Parsippany, NJ (US)

( * ) Notice: Subject to any disclaimer, the term of this patent is extended or adjusted under 35 U.S.C. 154(b) by 771 days.

(21) Appl. No.: 12/494,174

(22) Filed: Jun. 29, 2009

(65) Prior Publication Data

US 2010/0003300 A1 Jan. 7, 2010

Related U.S. Application Data

(60) Provisional application No. 61/076,454, filed on Jun. 27, 2008.

(51) Int. Cl.
| | |
|---|---|
| *A61K 9/14* | (2006.01) |
| *A61K 9/00* | (2006.01) |
| *A61K 9/50* | (2006.01) |
| *A61L 27/34* | (2006.01) |
| *A61L 31/10* | (2006.01) |

(52) U.S. Cl.
CPC ............. *A61K 9/0019* (2013.01); *A61K 9/5031* (2013.01); *A61L 27/34* (2013.01); *A61L 31/10* (2013.01); *A61L 2400/06* (2013.01)

(58) Field of Classification Search
USPC ....................................................... 424/489
See application file for complete search history.

(56) References Cited

U.S. PATENT DOCUMENTS

| | | |
|---|---|---|
| 3,266,987 A | 8/1966 | Crowley et al. |
| 4,460,563 A | 7/1984 | Calanchi |
| 4,794,000 A | 12/1988 | Ecanow |
| 5,360,610 A | 11/1994 | Tice |
| 5,650,173 A | 7/1997 | Ramstack et al. |
| 5,654,008 A | 8/1997 | Herbert et al. |
| 5,658,593 A | 8/1997 | Orly et al. |
| 5,811,272 A | 9/1998 | Snell et al. |
| 5,942,252 A | 8/1999 | Tice et al. |
| 5,989,463 A | 11/1999 | Tracy et al. |
| 6,131,211 A | 10/2000 | Hennessey |
| 6,235,224 B1 | 5/2001 | Mathiowitz et al. |
| 6,245,537 B1 | 6/2001 | Williams et al. |
| 6,440,493 B1 | 8/2002 | Gibson et al. |
| 6,537,586 B2 | 3/2003 | Lyons et al. |
| 6,540,393 B1 | 4/2003 | Lyons et al. |
| 6,548,569 B1 | 4/2003 | Williams et al. |
| 6,667,061 B2 | 12/2003 | Ramstack et al. |
| 6,669,961 B2 | 12/2003 | Kim et al. |
| 2005/0025809 A1* | 2/2005 | Hasirci et al. ................ 424/426 |
| 2006/0024379 A1* | 2/2006 | Brown et al. ................. 424/490 |
| 2006/0093771 A1 | 5/2006 | Rypacek |
| 2006/0246108 A1 | 11/2006 | Pacetti |
| 2007/0098736 A1* | 5/2007 | Cleland et al. ............ 424/185.1 |

FOREIGN PATENT DOCUMENTS

| | | |
|---|---|---|
| EP | 0610086 | 8/1994 |
| GB | 929401 | 6/1963 |
| WO | 9503036 | 2/1995 |
| WO | WO 99/32536 | 7/1999 |
| WO | 0101890 | 1/2001 |
| WO | 2005007195 | 1/2005 |
| WO | 2007092417 | 8/2007 |

OTHER PUBLICATIONS

Mundargi et al., "Development and evaluation of novel biodegradable microspheres based on poly(D,L-lactide-co-glycolide) and poly(ε-caprolactone) for controlled delivery of doxycycline in the treatment of human periodontal pocket: in vitro and in vivo studies", published online Jan. 24, 2007, Journal of Controlled Release, vol. 119, pp. 59-68.*

Mohamed, et al., "PLGA microcapsules with novel dimpled surfaces for pulmonary delivery of DNA", J Pharmaceutics, 311(1-2):97-107 (2006).

* cited by examiner

*Primary Examiner* — Michael B Pallay
(74) *Attorney, Agent, or Firm* — Pabst Patent Group LLP

(57) ABSTRACT

Compositions and methods of making and using of microparticle compositions that provide faster flow or improved injectability through smaller or small-diameter needles have been developed. Notably, the microparticle compositions can be successfully delivered or administered through smaller-diameter needles than other microparticle compositions prepared from biocompatible or biodegradable polymers including, for example, poly(lactide), poly(lactide-co-glycolide), polycaprolactone, or poly-3-hydroxybutyrate. The microparticle compositions can exhibit a higher solids loading for a given needle size and/or faster flow through needles than other microparticle compositions. Further, blending or mixing the polymer of the microparticle composition with other polymer formulations can enhance the injectability of the resulting formulation.

38 Claims, 5 Drawing Sheets

| Volume Statistics (Arithmetic) | | | (Untitled) |
|---|---|---|---|
| Calculations from 0.375 µm to 2000 µm | | | |
| Volume: | 100% | | |
| Mean: | 64.29 µm | S.D. | 27.27 µm |
| Median: | 58.28 µm | Variance: | 743.4 µm$^2$ |
| D (3,2): | 36.36 µm | Skewness: | 0.332 Right skewed |
| Mean/Median ratio: | 1.103 | Kurtosis: | -0.741 Platykurtic |
| Mode: | 105.9 µm | | |

$d_{10}$: 33.66 µm $d_{50}$: 58.28 µm $d_{90}$: 105.4 µm

| <10% | <25% | <50% | <75% | <90% |
|---|---|---|---|---|
| 33.66 µm | 43.87 µm | 58.28 µm | 86.07 µm | 105.4 µm |

Volume Statistics (Arithmetic) 00156-149_03.$I$

Calculations from 0.375 μm to 2000 μm

| | | | |
|---|---|---|---|
| Volume: | 100% | | |
| Mean: | 68.73 μm | S.D.: | 31.45 μm |
| Median: | 60.07 μm | Variance: | 989.2 $\mu m^2$ |
| D(3,2): | 56:61 μm | Skewness: | 0.929 Right skewed |
| Mean/Median ratio: | 1.144 | Kurtosis: | -0.108 Platykurtic |
| Mode: | 55.13 μm | | |

$d_{10}$: 36.43 μm $d_{50}$: 60.07 μm $d_{90}$: 126.1 μm

| <10% | <25% | <50% | <75% | <90% |
|---|---|---|---|---|
| 36.43 μm | 45.81 μm | 60.07 μm | 82.33 μm | 126.1 μm |

00256-146 + fraction 3

Volume Statistics (Arithmetic) 00256-146_03.$l$

Calculations from 0.375 μm to 2000 μm

| | | | |
|---|---|---|---|
| Volume: | 100% | | |
| Mean: | 67.59 μm | S.D.: | 41.24 μm |
| Median: | 55.39 μm | Variance: | 1701 $\mu m^2$ |
| D(3, 2): | 24.22 μm | Skewness: | 1.242 Right skewed |
| Mean/Median ratio: | 1.220 | Kurtosis: | 0.744 Leptakurtic |
| Mode: | 50.22 μm | | |

$d_{10}$: 31.62 μm $d_{50}$: 55.39 μm $d_{90}$: 152.4 μm

| <10% | <25% | <50% | <75% | <90% |
|---|---|---|---|---|
| 31.62 μm | 42.42 μm | 55.39 μm | 76.16 μm | 152.4 μm |

00256-146 + fraction 1,2,3

Volume Statistics (Arithmetic) (Untitled)

Calculations from 0.375μm to 2000μm

| | | | |
|---|---|---|---|
| Volume: | 100% | | |
| Mean: | 73.84μm | S.D.: | 41.29 μm |
| Median: | 64.43μm | Variance: | 1705 $\mu m^2$ |
| D (3,2): | 16.67 μm | Skewness: | 0.370 Right skewed |
| Mean/Median ratio: | 1.146 | Kurtosis: | -0.704 Platykurtic |
| Mode: | 127.6 μm | | |

$d_{10}$: 28.18μm $d_{50}$: 64.43μm $d_{90}$: 135.4 μm

| 10% | 25% | 50% | 75% | 90% |
|---|---|---|---|---|
| 28.18 μm | 43.99 μm | 64.43 μm | 107.3 μm | 135.4 μm |

INJECTABLE DELIVERY OF MICROPARTICLES AND COMPOSITIONS THEREFORE

CROSS-REFERENCE TO RELATED APPLICATIONS

The present application claims priority to U.S. Ser. No. 61/076,454 filed Jun. 27, 2008.

FIELD

The present invention relates to injectable microparticle compositions and compositions and methods of making, using, and kits thereof.

BACKGROUND

The diameter of a needle through which an injectable microparticle suspension is administered can be described in practical terms by both the outer diameter ("OD") of the needle itself and the inner diameter of the bore or opening inside the needle, which is referred to as the inside diameter ("ID") of the needle. The inside diameter of the needle must be large enough to permit a microparticle suspension to pass through without the microparticles clogging or otherwise blocking the flow of material through the needle. Additionally, the outside diameter of the needle must be appropriately sized for the particular application.

In the case of parenteral administration of a microparticle suspension, for example administration via a subcutaneous or intramuscular route, the outside diameter of the needle must be appropriately sized to minimize patient pain and discomfort to the extent possible given the clinical, surgical, medical, or pharmaceutical need. In other applications, the outside diameter of the needle must be appropriately sized to facilitate use or administration for the individual application. Often, pharmaceutical applications utilize needles in the range of 19 G to 30 G. "G" refers to the gauge or gauge number of the needle. The smaller the gauge number the larger the diameter of the needle. In other instances, such as infusions, surgical procedures, catheterization procedures, and other medical-device interventions, the outside diameter of the needle (tube) is limited by the equipment that is used to carry out a particular procedure. The needle can also vary in length as well as diameter.

There exists a balance between the inside and outside diameter of a needle that can be used to deliver a microparticle composition in a particular application. The inside diameter must be large enough to make an injection with ease and to avoid clogging, separation of the microparticles from the injection vehicle, failure to administer all microparticle sizes, or other blockages, while at the same time recognizing the need in the marketplace to use smaller-diameter needles to minimize patient pain and discomfort. Typically, smaller-diameter needles offer more versatility and practicality and are less painful to the subject.

Further, for a given size needle, it is desirable to be able to deliver greater quantities of the microparticle composition by administration of suspensions containing a higher solids content of the microparticle composition.

Syringability or injectability refers to the ability of an injectable microparticle suspension to flow through a small-diameter needle or device or, alternatively, for an injectable microparticle suspension to be successfully delivered, injected, or administered through a needle or device having a defined, small-diameter geometry. Several factors affecting injectability, and strategies to improve injectability are described in U.S. Pat. No. 6,667,061 to Ramstack et al.

Various strategies can be used to enhance, preserve, retain, or otherwise improve the injectability of microparticle suspensions. One strategy is to prepare smaller microparticles. Shifting the size range of the microparticle composition to a smaller particle size can improve injectability by simply lowering the potential for aggregates or other blockages in the needle. This approach may also allow for the use of smaller-diameter needles for administration. The use of smaller microparticles can be limiting, however, because smaller microparticles can have different medical or biological properties. For example, small microparticles, particularly those less than 10 microns in size, can be taken up by cells of the immune system (see U.S. Pat. No. 5,942,252 to Tice et al.) causing potentially unintended immunological responses in the subject and/or more rapid clearance by the reticuloendothelial ("RES") system, thereby decreasing the therapeutic effectiveness of the composition. In cases where cellular uptake is not the intended purpose, it may be undesirable to decrease the size of the microparticles.

Additionally, reducing the particle size of the microparticles can adversely affect the rate of release of the bioactive agent and the time-course, including duration over which the bioactive agent is released from the composition, making the resulting material undesirable for its intended use. For example, reducing the size or diameter of the microparticle can cause a bioactive agent to be released too quickly.

A second strategy that has been used to improve injectability of a microparticle suspension is to modify the properties of the injection vehicle itself. For example, injection vehicles having a high viscosity and a high concentration of surfactants have been used to improve the syringability or injectability of microparticle suspensions. See U.S. Pat. No. 6,667,061 to Ramstack et al. Similarly, U.S. Pat. No. 5,658,593 to Orly et al. describes the use of a viscous biocompatible carrier solution to aid in the injection or administration of a microparticle suspension. Injectable compositions are administered using an injection vehicle containing high concentrations of a viscosity-modifying agent, such as sodium carboxymethyl cellulose (CMC) or other types of polysaccharide viscosity-enhancing agents. However, such viscous compositions have several drawbacks including more pressure required for delivery, and thus more pain for the recipient.

Existing commercial microparticle products require the use of relatively large-diameter needles for their administration or delivery. Commercial pharmaceutical products that are administered as injectable microparticle suspensions include, among others, RISPERDAL® CONSTA® (risperidone), VIVITROL™ (naltrexone), and SANDOSTATIN LAR® (octreotide acetate) which, as indicated in the 2007 Physician's Desk Reference, are administered by 20-gauge thin-wall (20 G-TW), 20-gauge (20 G), and 19-gauge (19 G) needles, respectively, which have outside diameters in the range of about 0.035 inch to 0.042 inch (880-1070 microns) and inside bore diameters in the range of 0.023 inch to 0.0315 inch (580-800 microns). COAPTITE® (Boston Scientific), another microparticle product, is administered through a 21-G needle.

Commercial microparticle compositions, therefore, are typically administered using needles in the size of about 19 G to 21 G. These injectable microparticle compositions typically have particle sizes in the range of about 20-125 microns, with mean particle sizes of about 50-70 microns. The ratios of the inner diameter of the needles (19 G, 20 G, and 20 G-TW with inner diameters of 580-800 microns) to the microparticle diameter (60 microns) for these commercial formulations range from 9.6 to 13.0. Commercial microparticle compositions are typically administered in aqueous vehicles containing a viscosity-modifying agent and/or a surfactant. Suspensions of the microparticle composition in the injection vehicle are typically prepared at a concentration level in the range of about 10-40 wt % (percent solids).

The use of relatively large-diameter (small-gauge) needles, such as those described above, is undesirable to the patient because of pain and discomfort associated with the injection, which can affect patient compliance in maintaining and continuing an overall treatment program, including chronic treatment programs. Further, the aging population continues to support the need for patient care outside of the hospital or clinical settings, such as at-home and hospice (non-clinical) locations. The use of smaller-diameter needles allows administration of microparticle formulations in non-clinical settings by either the patient themselves, family members, or other at-home care-givers. This can improve the quality of life for patients by reducing pain and discomfort, thereby reducing or delaying the need for, frequency of, or duration of, in-patient care.

As a result, there exists a need for microparticle compositions which can be administered through, in relative terms, smaller-diameter needles, and in absolute terms, small diameter needles, without the disadvantages of the current methods of having to reduce the size of the microparticle or rely upon special injection vehicles.

It is therefore an object of the present invention to provide microparticle compositions which can be administered through, in relative terms, smaller-diameter needles, and in absolute terms, small needles, without the disadvantages of the current methods of having to reduce the size of the microparticle or rely upon special injection vehicles, methods of manufacture of such microparticle compositions, and uses thereof.

SUMMARY OF THE INVENTION

Microparticle compositions that provide faster flow, improved ease of injection, or improved injectability through, compared to commercially available compositions, smaller-diameter needles, and in absolute terms, small-diameter needles, and methods of making and using thereof are described herein. The microparticle compositions typically comprise a population of uniformly sized and shaped polymeric microparticles that exhibit faster flow or improved injectability when administered as suspensions through small-diameter needles. Higher microparticle concentrations, i.e., higher solids loading in the vehicle, can be achieved over reference microparticle compositions for the same needle inner diameter.

In one embodiment, microparticles formed of copolymers having a high percent of lactide and blends thereof demonstrate faster flow or improved injectability (e.g., as used herein, passage through a smaller diameter needle than microparticles formed from a homopolymer or blends of a copolymer with a low lactide content). In a preferred embodiment, the microparticles are prepared from: (1) a blend of poly(DL-lactide), e.g., poly(DL-lactide) and polycaprolactone; (2) a copolymer of DL- or L-lactide and caprolactone; (3) a copolymer of DL- or L-lactide, glycolide, and caprolactone; (4) a blend of any one or more of (1)-(3); or (5) a blend of any one or more of (1)-(3) with one or more additional biocompatible polymers, wherein (1)-(3) are different from the one or more additional biocompatible polymers.

In a particularly preferred embodiment, the microspheres are prepared from a blend of poly(DL-lactide) and poly(caprolactone), wherein the blend contains more than 0.1 wt. % and up to 30 wt. % polycaprolactone and from 70 wt. % to less than 100 wt. % poly(DL-lactide) or poly(L-lactide). In another embodiment, the microparticles are prepared from a copolymer of DL-lactide or L-lactide and caprolactone. These microparticles are characterized by nanotextured or “dimpled” surfaces that may result from immiscible polymer blends phase separating into identifiable domains. The dimples or nanotexturing may be concave or convex impressions or depressions on the surface of the microparticles or may be flat.

In another embodiment, the microparticles are formed of poly(4-hydroxybutyrate) (P4HB) or copolymers thereof.

In yet another embodiment, the microparticles are a mixture of these microparticles which exhibit desirable flow properties and the ability to pass through small needles and microparticles which do not share these properties when tested alone.

In one embodiment, the ratio of the needle inner diameter to the mean particle size is from 2.0 to 4.5, preferably from 2.5 to 4.5, more preferably from 3.0 to 4.5, most preferably from 3.9 to 4.2, and the solids content in the composition is from 10 wt. % to <30 wt. %. In another embodiment the ratio of the needle inner diameter to the mean particle size is from 4.0 to 8.0, more preferably from 4.5 to 8.0, most preferably from 4.5 to 7.6, and the solids content is ≥30 wt. %.

In another embodiment, the ratio of the needle inner diameter to the mean particle size is from 4.0 to 6.6 and the microparticle concentration is ≥30 wt. %. In a preferred embodiment, the ratio of the needle inner diameter to the mean particle size is from 3.0 to 4.2 and the microparticle concentration is from 10 wt. % to <30 wt. % or the ratio of the needle inner diameter to the mean particle size is from 4.0 to 5.7 and the microparticle concentration is ≥30 wt. %.

The microparticle compositions can be used for delivery of therapeutic, prophylactic or diagnostic agents. These may also be used to form coatings on a device, such as an implant, to provide improved surface properties, and/or improved surrounding flow properties.

BRIEF DESCRIPTION OF THE DRAWINGS

FIG. 1A is the size distribution test sample 1 FIG. 1B is the size distribution for test sample 2. FIG. 1C is the size distribution for test sample 3. FIG. 1D is the size distribution test sample 4 and FIG. 1E is the size distribution for test sample 5.

DETAILED DESCRIPTION OF THE INVENTION

I. Definitions

Figure 1A:
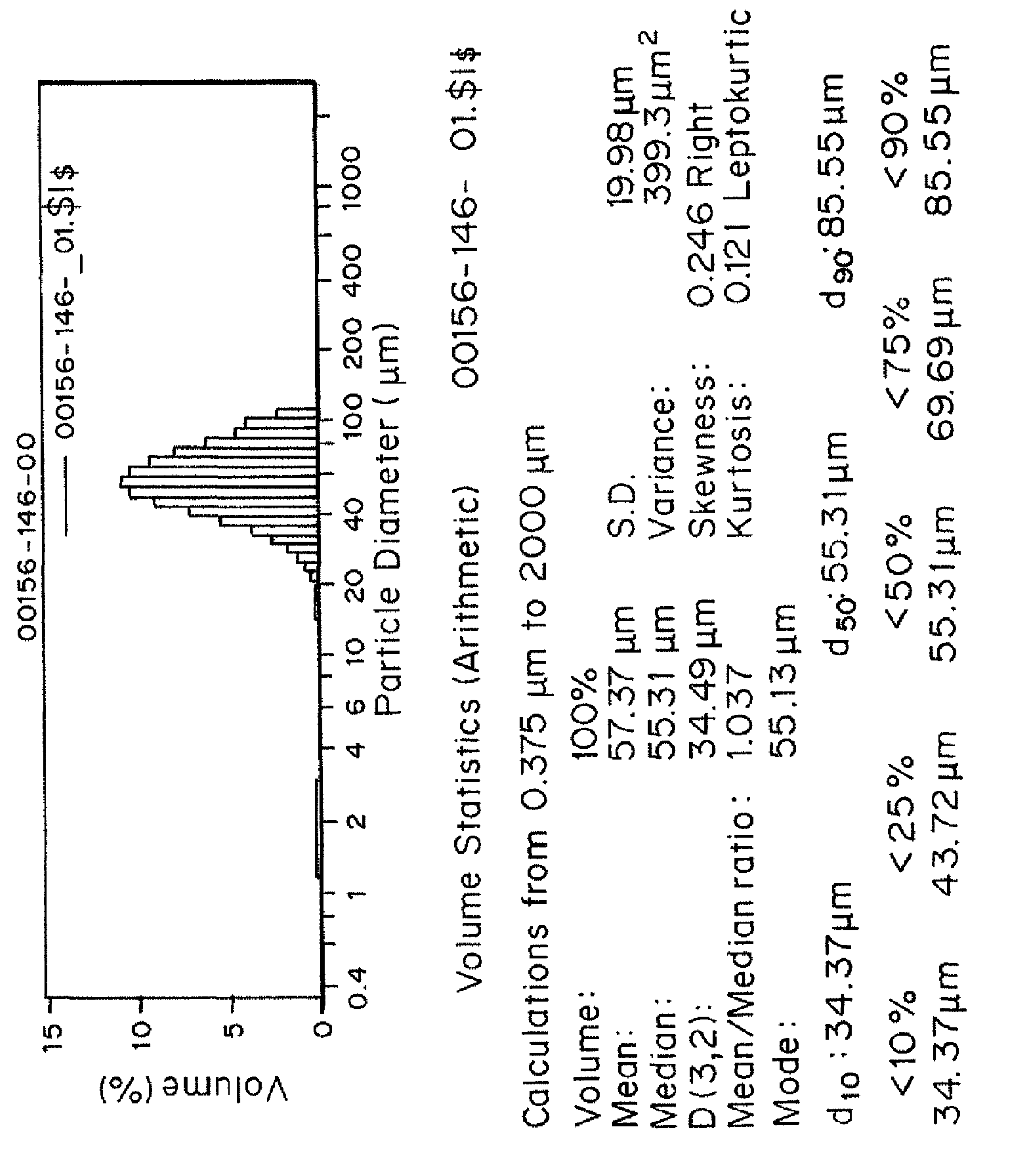
FIGS. 1A-1E show the particle size distribution (particle size (microns) versus volume (%)) for the five test samples in Example 23.

As used in the specification and the appended claims, the singular forms “a,” “an” and “the” include plural referents unless the context clearly dictates otherwise. Thus, for example, reference to “a vehicle” includes mixtures of two or more such vehicles.

“Optional” or “optionally” means that the subsequently described event, element, or circumstance may or may not occur, and that the description includes instances where the event or circumstance occurs and instances where it does not.

As used herein, a “wt. %” or “weight percent” or “percent by weight” of a component, unless specifically stated to the contrary, refers to the ratio of the weight of the component to the total weight of the composition in which the component is included, expressed as a percentage.

As used herein, a "mole percent" or "mole %" of a component, unless specifically stated to the contrary, refers to the ratio of the number of moles of the component to the total number of moles of the composition in which the component is included, expressed as a percentage.

"Contacting" means an instance of exposure by close physical contact of at least one substance to another substance.

"Admixture," "mixture," or "blend" is generally used herein to refer to a physical combination of two or more different components. In the case of polymers, an admixture, mixture, or blend of polymers is a physical blend or combination of two or more different polymers. The mixture may be homogeneous or heterogeneous.

"Bioactive agent" and "active agent" are used interchangeably include without limitation physiologically or pharmacologically active substances that act locally or systemically in the body. A biologically active agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment. Examples can include, but are not limited to, small-molecule drugs, peptides, proteins, antibodies, sugars, polysaccharides, nucleotides, oligonucleotides, aptamers, siRNA, nucleic acids, and combinations thereof. "Bioactive agent" includes a single such agent and is also intended to include a plurality of bioactive agents including, for example, combinations of two or more bioactive agents "Copolymer" is used herein to refer to a single polymeric material that is comprised of two or more different monomers. The copolymer can be of any form, such as random, block, graft, etc. The copolymers can have any end-group, including capped or acid end groups.

"Sufficient" or "effective" mean an amount and/or time needed to achieve one or more desired result.

"Biocompatible" as used herein refers to a material and any metabolites or degradation products thereof that are generally non-toxic to the recipient and do not cause any significant adverse effects to the subject.

"Biodegradable" refers to a material that will degrade or erode under physiologic conditions to smaller units or chemical species that are capable of being metabolized, eliminated, or excreted by the subject.

"PHA", as used herein, refers to "polyhydroxyalkanoate."

"Poly-4-hydroxybutyrate" or "poly(4-hydroxybutyrate)" as used herein refers to a polyhydroxyalkanoate homopolymer comprising 4-hydroxybutyrate units. It can also be referred to as TEPHAFLEX® polymer, TEPHAFLEX®, P4HB or PHA4400. P4HB can be prepared synthetically or from biologically sources, such as bacteria and plants.

"Copolymers of poly-4-hydroxybutyrate" as used herein refers to any polymers containing 4-hydroxybutyrate with one or more different hydroxy acid units. These copolymers may be prepared synthetically or from biological sources, such as bacteria and plants.

"Poly-4-hydroxybutyrate-co-3-hydroxybutyrate" as used herein refers to a polyhydroxyalkanoate copolymer containing 4-hydroxybutyrate units and 3-hydroxybutyrate units. It can be referred to as P4HB3HB, TEPHELAST® copolymer, or TEPHELAST®. The % following the polymer refers to the mole-percent of the 4-hydroxybutyrate monomer. TEPHELAST® copolymer can be prepared synthetically or from biological sources, such as bacteria or plants, and is obtainable from Tepha, Inc.

DL-PLG is poly(DL-lactide-co-glycolide) prepared from the indicated mole ratios of DL-lactide and glycolide, respectively. L-PLG is poly(L-lactide-co-glycolide) prepared from the indicated mole ratios of L-lactide and glycolide, respectively. DL-PL is poly(DL-lactide). L-PL is poly(L-lactide). D-PL is poly(D-lactide). Poly(lactide-co-glycolide), as used herein, refers to poly(DL-lactide-co-glycolide), poly(D-lactide-co-glycolide), and poly(L-lactide-co-glycolide).

PCL is polycaprolactone. DL-lactide/caprolactone is a copolymer prepared from the indicated mole ratios of DL-lactide and caprolactone, respectively. The copolymer can be random or block. L-lactide/caprolactone is a copolymer prepared from the indicated mole ratios of L-lactide and caprolactone, respectively. The copolymer can be random or block.

DL-G-CPL is a copolymer prepared from the indicated mole ratios of (DL-lactide):glycolide:caprolactone, respectively. The copolymer can be a random or block copolymer.

TephELAST® is poly(4-hydroxybutyrate-co-3-hydroxybutyrate) copolymer containing the indicated mole-percent of the 4-hydroxybutyrate monomer, with the balance of mole percent being 3-hydroxybutyrate, prepared synthetically or from biological sources, such as bacteria or plants, obtainable from Tepha, Inc.

"Molecular weight" as used herein, unless otherwise specified, refers to the relative average chain length of the bulk polymer. In practice, molecular weight can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

"Mean particle size" refers to the statistical mean particle size (diameter) of the particles in the composition.

D(90) or $D_{90}$ is the particle size (diameter) at the $90^{th}$-percentile of the particle size distribution in the composition, which serves as an indicator of the size range on the upper end of the particle size distribution.

"Controlled release" or "modified release", as used herein, refers to a release profile in which the drug release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

"Excipient" is used herein to include any other compound that can be contained in or on the microparticle that is not a therapeutically or biologically active compound. As such, an excipient should be pharmaceutically or biologically acceptable or relevant, for example, an excipient should generally be non-toxic to the subject. "Excipient" includes a single such compound and is also intended to include a plurality of compounds.

The term "microparticle" is used herein to refer to structures or particles having sizes from about 10 nm to about 1000 microns and includes microcapsules, microspheres, nanoparticles, nanocapsules, nanospheres, as well as particles, in general that are less than about 1000 microns. In one embodiment, the particles have a mean size of less than about 90 microns, preferably less than about 80 microns, more preferably from about 50 to about 80 microns. In other embodiments, the particles have a mean size from about 30 to about 50 microns.

In another embodiment, the particles have a $D_{90}$ of less than 120 microns, preferably less than 110 microns, and more preferably less than 100 microns. In a preferred embodiment, the particles have a $D_{90}$ of about 90 microns. In other embodiments, the particles have a $D_{90}$ of about 30 to about 50 microns, preferably from about 30 to 40 microns.

The particles may be spherical or non-spherical in shape. A microcapsule or nanocapsule is generally a particle that has a heterogeneous structure whereby the particle is covered by a substance or coating of some type, often a polymer or polymeric material or a wall-forming material. When the particle contains an agent (such as a bioactive agent or other excipient or additive), the agent is generally heterogeneously distributed in the particle and is typically centrally located within the membrane or coating. A microcapsule can also include microbubbles (hollow particle), porous microbubbles, porous microcapsules, and particles in general that comprise a central core surrounded by a unique outer membrane. In contrast, a microsphere or nanosphere has a more homogeneous structure whereby any incorporated agents are more or less distributed throughout the matrix of the particle where the remainder of the matrix is comprised of a polymer or polymeric material or matrix-forming material. A microsphere or nanosphere can include porous microspheres or nanospheres.

As used herein, "solids content" refers to the weight percent of particles suspended in a liquid vehicle, calculated as weight of the particles divided by weight of the particles and vehicle.

"Needle" is used herein to refer to devices that can be used to administer, deliver, inject, or otherwise introduce a microparticle formulation to a subject for any purpose(s) including medical, clinical, surgical, therapeutic, pharmaceutical, pharmacological, diagnostic, cosmetic, and prophylactic purposes. Thus, as defined herein, needle includes needle, all needle-like devices, and all other annular microparticle introduction devices, such as tubing, etc. Specific examples include needles, hypodermic needles, surgical needles, infusion needles, catheters, trocars, cannulas, tubes, and tubing used for clinical, surgical, medical, procedural, or medical purposes.

"Injected", "injection", or "injectability" as used herein is intended to include any administration of the microparticle, such as by injection, infusion, or any other delivery through any annular delivery device to the subject. Injection includes delivery through a tube.

The term "gauge" refers to the needle size in terms of a gauge scale. A lower gauge number indicates a larger inner diameter. Gauge size versus the needle inner diameter is typically standardized but some variations can occur.

The outer and inner diameter of the needle, expressed in inches and millimeters, for gauge sizes described herein are from the 2007 Product Guide for BD Precision Glide™ hypodermic needle tubing specifications, and are shown in Table 1.

TABLE 1

Gauge size versus outer diameter (OD) and inner diameter (ID) for BD Precision Glide ™ hypodermic needles.

| | O.D. | | Regular I.D. ("G") | | Thin Wall I.D. ("TW") | |
|---|---|---|---|---|---|---|
| Gauge | (Inches) | (MM) | (Inches) | (MM) | (Inches) | (MM) |
| 30 | 0.0120 | 0.3048 | 0.0060 | 0.1524 | 0.0070 | 0.1778 |
| 29 | 0.0130 | 0.3302 | 0.0070 | 0.1778 | 0.0080 | 0.2032 |

TABLE 1-continued

Gauge size versus outer diameter (OD) and inner diameter (ID) for BD Precision Glide ™ hypodermic needles.

| | O.D. | | Regular I.D. ("G") | | Thin Wall I.D. ("TW") | |
|---|---|---|---|---|---|---|
| Gauge | (Inches) | (MM) | (Inches) | (MM) | (Inches) | (MM) |
| 28 | 0.0140 | 0.3556 | 0.0070 | 0.1778 | 0.0080 | 0.2032 |
| 27 | 0.0160 | 0.4064 | 0.0075 | 0.1905 | 0.0100 | 0.2540 |
| 26 | 0.0180 | 0.4572 | 0.0095 | 0.2413 | 0.0120 | 0.3048 |
| 25 | 0.0200 | 0.5080 | 0.0095 | 0.2413 | 0.0120 | 0.3048 |
| 24 | 0.0220 | 0.5588 | 0.0115 | 0.2921 | 0.0140 | 0.3556 |
| 23 | 0.0250 | 0.6350 | 0.0125 | 0.3175 | 0.0150 | 0.3810 |
| 22 | 0.0280 | 0.7112 | 0.0155 | 0.3937 | 0.0180 | 0.4572 |
| 21 | 0.0320 | 0.8128 | 0.0195 | 0.4953 | 0.0220 | 0.5588 |
| 20 | 0.0350 | 0.8890 | 0.0230 | 0.5842 | 0.0255 | 0.6477 |
| 19 | 0.0420 | 1.0668 | 0.0270 | 0.6858 | 0.0315 | 0.8001 |
| 18 | 0.0500 | 1.2700 | 0.0330 | 0.8382 | 0.0380 | 0.9652 |
| 17 | 0.0590 | 1.4986 | 0.0410 | 1.0414 | 0.0460 | 1.1684 |
| 16 | 0.0650 | 1.6510 | 0.0470 | 1.1938 | 0.0520 | 1.3208 |

"Modified release" as used herein refers to a composition for which the drug release characteristics of time, course and/or location are chosen to accomplish therapeutic or convenience objectives not offered by conventional dosage forms such as solutions, ointments, or promptly dissolving dosage forms. Immediate release, delayed release, extended release, and pulsatile release and their combinations are types of modified release.

"Delayed release" as used herein refers to release of a drug (or drugs) at a time other than promptly after administration.

"Extended release" as used herein refers to release of a drug (or drugs) that allows at least a twofold reduction in dosing frequency as compared to the drug presented as a conventional dosage form (e.g. as a solution or prompt drug-releasing, conventional solid dosage form).

"Pulsatile release" as used herein refers to release of a drug (or drugs) that mimics a multiple dosing profile without repeated dosing and allows at least a twofold reduction in dosing frequency as compared to the drug presented as a conventional dosage form (e.g. as a solution or prompt drug-releasing, conventional solid dosage form). A pulsatile release profile is characterized by a time period of no release (lag time) or reduced release followed by rapid drug release.

II. Microparticle Compositions

Microparticle compositions prepared from a particular polymer, polymers, or polymer admixtures (blends) whereby the resulting microparticles exhibit faster flow and/or improved injectability through small-diameter devices such as needles, trocars, catheters, tubes are described herein. The improved injectability of a microparticle composition refers to the flow or administration of the microparticle composition after preparing a suspension of the composition in a suitable liquid suspending medium or injection vehicle. The improved flow characteristics of the resulting suspension formed from microparticle compositions allows administration through needles and can also allow administration of higher concentration suspensions.

Microparticle compositions that provide faster flow or improved injectability through, compared to commercially available compositions, and methods of making and using thereof are described herein. The microparticle compositions contain polymeric microparticles that exhibit faster flow or improved injectability when administered as suspensions through needles. Higher microparticle concentrations, i.e., higher solids content in the vehicle, can be achieved over the reference microparticle compositions for the same needle inner diameter.

In one embodiment, microparticles formed of copolymers having a high lactide content and blends thereof demonstrate faster flow or improved injectability (i.e., as used herein, passage through a needle than microparticles formed from a homopolymer or not a blend of a copolymer with a high lactide content). In a preferred embodiment, the microspheres are prepared from: (1) a blend of poly(DL-lactide) and polycaprolactone; (2) a copolymer of DL- or L-lactide and caprolactone; (3) a copolymer of DL- or L-lactide, glycolide, and caprolactone; (4) a blend of any one or more of (1)-(3); or (5) a blend of any one or more of (1)-(3) with one or more additional biocompatible polymers, wherein (1)-(3) are different from the one or more additional biocompatible polymers.

In a particularly preferred embodiment, the microparticles are prepared from a blend of poly(DL-lactide) and poly(caprolactone), wherein the blend contains more than 0.1 wt. % and up to 30 wt. % polycaprolactone and from 70 wt. % to less than 100 wt. % poly(DL-lactide) or poly(L-lactide). In another embodiment, the microspheres are prepared from a copolymer of DL-lactide or L-lactide and caprolactone. These microparticles are characterized by nanotextured or "dimpled" surfaces that may result from immiscible polymer blends phase separating into identifiable domains. In one embodiment, the particles contain dimples having diameters from about 10 to about 900 nanometers, preferably from about 10 to about 600 nm, more preferably from about 10 to about 500 nm, more preferably from about 10 to about 250 nm, most preferably from about 10 to about 100 nm and/or nanotexturing on the surface. If the surface is nanotextured, the percent of the surface textured in one embodiment is at least 0.5%, preferably at least 1.0%, more preferably 2.5%, most preferably at least 5%. In another embodiment, the percent of the surface that is textured is from about 0.5% to about 30%, preferably from about 0.5% to about 20%, more preferably from about 0.5% to about 15%, and most preferably from about 0.5% to about 10%. In one embodiment, the particles have substantially uniform dimpling and/or texturing. In another embodiment, the microparticles are formed from copolymers comprising lactide and caprolactone.

In another embodiment, the microparticles are formed of P4HB or copolymers thereof. These are not typically characterized by dimpling but have advantageous flow and injectability properties.

In yet another embodiment, the microparticles are a mixture of the microparticles which exhibit desirable flow properties and the ability to pass through needles and microparticles which do not share these properties when tested alone.

In one embodiment, the ratio of the needle inner diameter to the mean particle size is from 2.0 to 4.5, preferably from 2.5 to 4.5, more preferably from 3.0 to 4.5, most preferably from 3.9 to 4.2, and the solids content in the composition is from 10 wt. % to <30 wt. %. In another embodiment the ratio of the needle inner diameter to the mean particle size is from 4.0 to 8.0, more preferably from 4.5 to 8.0, most preferably from 4.5 to 7.6, and the solids content is ≥30 wt. %.

In another embodiment, the ratio of the needle inner diameter to the mean particle size is from 4.0 to 6.6 and the microparticle concentration is ≥30 wt. %. In a preferred embodiment, the ratio of the needle inner diameter to the mean particle size is from 3.0 to 4.2 and the microparticle concentration is from 10 wt. % to <30 wt. % or the ratio of the needle inner diameter to the mean particle size is from 4.0 to 5.7 and the microparticle concentration is ≥30 wt. %.

Calculated ratios for needle inner diameter:mean particle diameter ($D_{90}$), assuming regular-wall BD-brand needles except where noted, are shown in Table 2.

TABLE 2

Calculated ratios of needle inner diameter:particle diameter

| Particle diameter, microns | 20G | 21G | 23G | 25G | 25G-TW* |
|---|---|---|---|---|---|
| 40 | 14.6 | 12.4 | 7.95 | 6.02 | 7.62 |
| 50 | 11.7 | 9.90 | 6.36 | 4.82 | 6.10 |
| 60 | 9.73 | 8.25 | 5.30 | 4.02 | 5.08 |
| 70 | 8.34 | 7.07 | 4.54 | 3.44 | 4.36 |
| 80 | 7.30 | 6.19 | 3.98 | 3.01 | 3.81 |
| 90 | 6.49 | 5.50 | 3.53 | 2.68 | 3.39 |
| 100 | 5.84 | 4.95 | 3.18 | 2.41 | 3.05 |
| 110 | 5.31 | 4.50 | 2.89 | 2.19 | 2.77 |
| 115 | 5.08 | 4.30 | 2.76 | 2.10 | 2.65 |
| 120 | 4.87 | 4.12 | 2.65 | 2.01 | 2.54 |

*"TW" refers to thin-walled needles

Microparticle compositions can be used in a variety of applications. In one aspect, the microparticle compositions contain one or more bioactive agents. As such, the microparticles allow for the modified release of one or more bioactive agents. Examples of modified release include immediate release, delayed release, extended release, pulsatile release, and combinations thereof. In another aspect, the microparticle compositions contain no bioactive agents and can be used in a variety of medical, surgical, clinical, cosmetic, and medical device purposes.

A. Polymers

Polymers, copolymers, or combination (blends or admixtures) of polymers that, when used to prepare microparticles, provide the improved flow properties and/or microparticle injectability (or flow characteristics) as described herein. The microparticles can be formed from homopolymers, copolymers or blends containing two or more polymers, such as homopolymers or copolymers or combinations thereof.

1. Blends

In one embodiment, the polymer is a polyester or a blend or blends of polyesters. Polyester as used herein refers to polymers that contain the monomer unit:

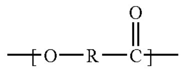

wherein R is a linear or branched, aliphatic or aromatic group.

In a preferred embodiment, the microparticles are formed from a biocompatible polymer containing (1) a blend of poly(DL-lactide) and polycaprolactone; (2) a copolymer of DL-lactide or L-lactide and caprolactone; (3) a copolymer of DL-lactide or L-lactide, glycolide, and caprolactone; (4) poly(4-hydroxybutyrate-co-3-hydroxybutyrate); (5) a blend of any one or more of (1)-(4); or (6) a blend of any one or more of (1)-(4) with one or more additional biocompatible polymers, wherein the polymers in (1)-(4) are different from the one or more additional biocompatible polymers.

Other biocompatible or biodegradable polymers that can be blended with the polymers described above include, but are not limited to, poly(lactides); poly(glycolides); poly(lactide-co-glycolides); poly(lactic acid); a poly(glycolic acid); poly(lactic acid-co-glycolic acids); polycaprolactones; poly(orthoesters); polyanhydrides; poly(phosphazenes); polyhydroxyalkanoates; poly(hydroxybutyrates); synthetically or biologically prepared polyesters; poly(lactide-co-caprolactones); polycarbonates; tyrosine polycarbonates; polyamides (including synthetic and natural polyamides, polypeptides, and poly(amino acids)); polyesteramides; polyesters; poly (dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/ poly(oxypropylene) copolymers; polyacetals, polyketals; polyphosphates; (phosphorous-containing) polymers; polyphosphoesters; polyhydroxyvalerates; polyalkylene oxalates; polyalkylene succinates; poly(maleic acids); chitin; chitosan; modified chitosan; biocompatible polysaccharides derivatized polysaccharides (jointly referred to herein as polysaccharides); and combinations thereof (including blends and block, random, or graft copolymers thereof). In one embodiment, copolymers that can be used include block copolymers containing blocks of hydrophilic or water soluble polymers, such as polyethylene glycol, (PEG) or polyvinyl pyrrolidone (PVP), with blocks of other biocompatible or biodegradable polymers, for example, poly(lactide), poly (lactide-co-glycolide, or polycaprolactone or combinations thereof.

Suitable biocompatible, non-biodegradable polymers include, but are not limited to, polyacrylates; ethylene-vinyl acetates; acyl substituted cellulose acetates; non-degradable polyurethanes; polystyrenes; polyvinyl chlorides; polyvinyl fluorides; poly(vinyl imidazoles); chlorosulphonate polyolefins; polyethylene oxides; or blend or copolymers thereof.

In one embodiment, the polymer is a biodegradable polyester containing monomers such as glycolide and/or lactide including polyglycolide, polylactide, and poly(lactide-co-glycolide) or mixtures thereof. These polymers are available with or without carboxylic acid end groups. When the end group of the poly(lactide-co-glycolide), poly(lactide), or polyglycolide is not a carboxylic acid, for example, an ester, then the resultant polymer is referred to herein as blocked or capped. The unblocked polymer, conversely, has a terminal carboxylic group (herein referred to as having an acid end-group). In one embodiment, linear lactide/glycolide polymers are used; however star polymers can be used as well. In certain aspects, high molecular weight polymers can be used for medical devices, for example, to meet strength requirements. In other aspects, low or medium molecular weight polymers can be used for drug-delivery and vaccine delivery products where resorption time and not material strength is more important. The lactide portion of the polymer has an asymmetric carbon. Racemic DL-, L-, and D-polymers are commercially available. The L-polymers are more crystalline and resorb slower than DL-polymers. In addition to copolymers containing glycolide and DL-lactide or L-lactide, copolymers of L-lactide and DL-lactide are also available.

In embodiments where the biodegradable polymer is poly (lactide-co-glycolide), poly(lactide), or poly(glycolide), the amount of lactide and glycolide in the polymer may vary. In one aspect, the biodegradable polymer contains 0 to 100 mole %, 40 to 100 mole %, 50 to 100 mole %, 60 to 100 mole %, 70 to 100 mole %, 80 to 100 mole %, 60-80 mole %, or 60-70 mole % lactide and from 0 to 100 mole %, 0 to 60 mole %, 0 to 50 mole %, 0 to 40 mole %, 0 to 30 mole %, 0 to 20 mole %, 20 to 40 mole %, or 30 to 40 mole % glycolide, wherein the total amount of lactide and glycolide is 100 mole %. In specific aspects, the biodegradable polymer can be poly(DL-lactide or L-lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), wherein the ratios are mole ratios.

In a preferred embodiment, the microparticles can be formed from blends or mixtures (admixtures) of poly(DL-lactide) (DL-PL) or poly(L-lactide) (L-PL) and polycaprolactone (PCL) or compositions containing of blends of DL-PL and PCL that are further blended with one or more additional suitable biocompatible and optionally biodegradable polymers such as, for example, poly(DL-lactide-co-glycolide); poly(DL-lactide); or a polyhydroxyalkanoate ("PHA"), such as poly 3-hydroxy hydroxybutyrate, poly 4-hydroybutyrate, or poly (4-hydroxybutyrate-co-3-hydroxybutyrate).

In embodiments where the microparticle composition is prepared from blends or mixtures of polylactide and polycaprolactone, the concentration of PCL in the blend is from greater than 0 wt % up to about 50 wt %, preferably greater than 0.1 wt. % up to about 50 wt. % polycaprolactone and the concentration of polylactide in the blend is from about 50 wt. % to less than 100 wt. % DL-lactide or L-lactide. In specific aspects, the admixture can be, for example, 50% wt. % DL-PL and 50 wt. % of a PCL; 70% by weight of a DL-PL and 30% by weight of a PCL; 80% by weight of a DL-PL and 20% by weight of a PCL; 90% by weight of a DL-PL and 10% by weight of a PCL; or 95% by weight of a DL-PL and 5% by weight of a PCL.

In embodiments where the microparticle composition is formed from blends of polylactide and polycaprolactone that are further blended with other suitable biocompatible and optionally biodegradable polymers, the blend may contain from 0 to 99.9% of the biocompatible polymer with the remainder being a blend or admixture of polylactide and polycaprolactone, where the ratio of polylactide to polycaprolactone is at least 50% polylactide. In one embodiment, microparticles are formed from a blend containing a combination of DL-PL and PCL that is further blended with a larger amount of a poly(DL-lactide-co-glycolide) (DL-PLG). In a preferred embodiment, the microparticle composition contains about 7.5 wt. % DL-PL and 2.5 wt. % PCL along with about 90 wt. % of a 75:25 DL-PLG or 25 wt. % of a 95/5 wt. % DL-PL/PCL mixture along with 75 wt. % DL-PLG. Additional examples include, but are not limited to, microparticles prepared from 80% PLG and 20% of a mixture of PL and PCL; microparticles prepared from 60% PLG and 40% of a mixture of PL and PCL; and compositions containing 40% PLG and 60% of a mixture of PL and PCL.

In one embodiment, the biodegradable polymer is a polyester, poly(lactide-co-glycolide), polylactide, polyglycolide, polycaprolactone, or a copolymer thereof, having an intrinsic viscosity of from 0.05 to 7.0 dL/g, 0.05 to 1.5 dL/g, 0.05 to 1.2 dL/g, 0.15 to 1.5 dL/g, 0.15 to 1.0 dL/g, 0.15 to 0.8 dL/g, 0.15 to 0.6 dL/g, or 0.15 to 0.4 dL/g as measured in chloroform at a concentration of 0.5 g/dL at 30° C.

The polymer blends can also be prepared from two or more microparticle formulations. In another aspect, microparticle compositions that differ in particle size can be blended together. The microparticle compositions that are blended can be similar in composition except for particle size or they can differ in composition and particle size. Microparticle compositions that are blended together can differ in a variety of ways, for example, polymer molecular weight, inherent viscosity, polymer composition (copolymer composition or the composition of a polymer admixture), choice of bioactive agent, concentration of bioactive agent, choice of excipient, concentration of excipient, distribution of agent in the particle, or any combination thereof.

2. Copolymers

The microparticle compositions can also be prepared from copolymers. In one embodiment, the microparticles compositions are prepared from a copolymer of DL-lactide or L-lactide and caprolactone or DL-lactide, glycolide, and caprolactone. The copolymer can contain from about 25 to about 98 mole % DL or L-lactide and from about 75 to about 2 mole % caprolactone, such as for example, about 75 mole % DL or L-lactide and about 25 mole % caprolactone or about 90 mole % DL or L-lactide and 10 mole % caprolactone.

In another embodiment, the copolymer can be about 25-98 mole % DL- or L-lactide and about 2-75 mole % caprolactone, about 2-50 mole % caprolactone, about 2-30 mole % caprolactone, or about 6 mole % caprolactone wherein the remainder of the copolymer composition, about 0-75 mole % is glycolide, about 0-49 mole % is glycolide, or about 24 mole % is glycolide. Specific examples include 70 wt. % DL-lactide or L-lactide, 24 wt. % G and 6 wt. % CPL; 67 mole % DL- or L-lactide and 25 mole % caprolactone wherein the remainder of the copolymer composition, about 8 mole %, is glycolide; 38 mole % DL-lactide and 34 mole % caprolactone wherein the remainder of the copolymer composition (about 34%) is glycolide; and 38 mole % DL- or L-lactide, 24 mole % caprolactone and 38 mole % glycolide.

The copolymers can also be block copolymers further containing blocks of either hydrophobic or hydrophilic biocompatible polymers or biopolymers or biodegradable polymers including, but not limited to, polyethers (e.g., polyethylene glycol, (PEG)), polyvinyl pyrrolidone (PVP), polysaccharaides, polylactides, polyesters, and combinations thereof.

The copolymers can be admixed or blended with other suitable biocompatible polymers or biopolymers or biodegradable polymers such as poly(DL-lactide-co-glycolide) or polyhydroxyalkanoates (PHAs), such as P4HB3HB among others. In one embodiment, the microparticle composition contains 90% by weight of a 75:25 DL-PLG blended with about 10% by weight of a copolymer containing about 38 mole % DL-lactide and 38 mole % caprolactone, wherein the remainder of the copolymer composition (about 34 mole %) is glycolide. In another embodiment, the microparticle composition contains 25 wt. % of 70:24:6 DL-G-CPL admixed with 75 wt. % of a 75-25 DL-PLG.

The microparticles can also be formed from copolymers of 4HB, such as the copolymer poly-4-hydroxybutyrate-co-3-hydroxybutyrate. Poly-4-hydroxybutyrate-co-3-hydroxybutyrate ("P4HB3HB" or TEPHELAST® copolymer) is a PHA thermoplastic copolymer that is produced by a fermentation process (see U.S. Pat. No. 6,548,569 to Williams et al.). P4HB3HB is produced by Tepha, Inc. (Lexington, Mass.) under the tradename TEPHELAST®. Methods to control molecular weight of PHA polymers are disclosed in U.S. Pat. No. 5,811,272 to Snell et al., and methods to purify PHA polymers for medical use are disclosed in U.S. Pat. No. 6,245,537 to Williams et al. PHAs with degradation rates in vivo of less than one year are disclosed in U.S. Pat. No. 6,548,569 to Williams et al. and PCT WO 99/32536 to Martin et al. Other suitable 4HB copolymers include copolymers of other hydroxyl acids, such as 3-hydroxy acids in addition to or in place of 3HB, 5-hydroxy acids, lactic acid, glycolic acid, and combinations thereof.

Typically, the 4-hydroxybutyrate is present in an amount from about 2 to about 40 mole %, preferably from about 20 to about 30 mole %, and the 3-hydryoxybutryate is present in an amount from about 98 to about 60 mole %, preferably from about 80 to about 70 mole % in the P4HB3HB copolymer. In a preferred embodiment, a copolymer containing 30 mol. % 4-hydroxybutyrate and 70 mol. % 3-hydroxybutyrate is used to prepare the microparticles.

Microparticles can be also be prepared from polymer blends of poly-4-hydroxybutyrate-co-3-hydroxybutyrate along with other biocompatible polymers and optionally biodegradable polymers, such as for example, poly(DL-lactide-co-glycolide) or poly(DL-lactide), among others. In specific examples, a microparticle composition is prepared from an admixture comprising greater than 0 wt %, at least 5 wt. %, 10 wt. %, at least 10 wt. %, at least 15 wt. %, at least 20 wt. %, at least 25 wt. %, or up to less than 100 wt. %, P4HB3HB copolymer and less than 100 wt. %, less than or equal to 95 wt. %, 90 wt. %, less than 90 wt. %, ≤85 wt. %, ≤80 wt. %, ≤75 wt. %, or greater than 0 wt. % of a 75:25 DL-PLG. In further aspects, the admixture is 10 wt. % P4HB3HB copolymer and 90 wt. % of a 75:25 DL-PLG; 25% wt. P4HB3HB and 90 wt. % of a 75:25 DL-PLG; 10 wt. % P4HB3HB and 90 wt. % of 65:35 DL-PLG; 10 wt. % P4HB3HB and 90 wt. % DL-PL; or 25 wt. % P4HB3HB and 75 wt. % DL-PL.

The use of the particular polymers described above in the preparation of microparticles allows for the use of a needle having a higher gauge number compared to a reference composition, where all other variables are held essentially constant. To compare such an effect, the polymers can be compared to a reference polymer, such as 75:25 poly(DL-lactide-co-glycolide), poly(DL-lactide), polycaprolactone, or poly (4-hydroxybutyrate). The first and second microparticle compositions differ only by or essentially only by their polymeric compositions so that the compositions can be compared to the reference polymer.

3. Addition of Caprolactone-Based Compounds

Caprolactone-based compounds may be added to the base polymer(s) or monomer(s) to improve the injectability of the microparticle composition through a needle. The caprolactone-based compound can be a polycaprolactone oligomer or polymer, such as PCL, added to the base polymer, e.g., polylactide or poly(lactide-co-glycolide). In one embodiment, polycaprolactone is blended with polylactide, wherein the blend contains at least 80% polylactide. In a preferred embodiment, the ratio of polylactide to polycaprolactone is 95:5. In another embodiment, PL-rich blends of PL and PCL are blended with another polymer, as PLG, to form a mixture that is at least about 5% PL-rich blend of PL and PCL. In a preferred embodiment, the concentration of the PL-rich blend of PL and PCL is 5% or 10% by weight of the blend with PLG.

The caprolactone-based compound can also be a caprolactone based monomer, which is copolymerized with one or more base monomers such as DL-lactide or L-lactide, and optionally glycolide. Even the addition of a small amount of caprolactone can provide a benefit to the base polymer or monomer in improving the injectability. By improved injectability, it is meant that, a needle having a higher gauge or a higher microparticle concentration can be used for successful injection for the same size microparticles.

Without being bound by any one hypothesis, one explanation is that the microparticle compositions form unique surface morphology, upon addition of a caprolactone-based compound, which facilitates the improved flow properties observed. This surface morphology may also induce desired properties in the liquid phase near the surface of the microparticles, to achieve smooth flow of the microparticles.

B. Microparticle to Needle Inner Diameter Ratio

In one embodiment, methods for delivering a microparticle to a subject including (a) providing a microparticle composition containing microparticles in a fluid, wherein the microparticle are formed of a first biocompatible polymer and optionally one or more additional biocompatible polymers, and wherein the microparticle composition has a mean particle size and a microparticle concentration, and (b) successfully injecting the microparticle composition through a needle into the subject. In a preferred embodiment, the first and the one or more additional biocompatible polymers are different.

In one embodiment, the ratio of the needle inner diameter to the mean particle size is from X to Y and the microparticle concentration is from 10 wt. % to <30 wt. % or (2) the ratio of the needle inner diameter to the mean particle size is from A to B and the microparticle concentration is ≥30 wt. %, wherein X is 2.0 and Y is 4.5, including 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, and 4.5. A 4.0 and B is 8.0, including 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0.

Thus, where all other variables are held constant, such as the microparticle concentration, mean particle size, D(90) particle size, vehicle (fluid) type, use or non-use of a surfactant, type of surfactant, etc., the compositions and methods described herein allow for the use of a needle having a higher gauge value than conventional microparticle compositions. Also, if all other variables are held constant, for the same size needle, the compositions and methods described herein allow for a higher concentration of microparticles in the vehicle or fluid while maintaining a successful injection.

In various embodiments, X is 3.0, Y is 4.5, A is 4.0, and B is 8.0; X is 3.0, Y is 4.2, A is 4.0, and B is 5.7; or X is 3.0, Y is 3.8, A is 4.0, and B is 4.8. The microparticle solids content in these embodiments can be from about less than <1% to about 30 wt. % to 40, 45, 50, 55, or 60 wt. %. In a preferred embodiment, X is 3.0, Y is 3.8, A is 4.0, B is 4.8 and the microparticle concentration is from 30 to 50 wt. %.

C. Bioactive Agents

The microparticles can be used to deliver one or more therapeutic, diagnostic, or prophylactic agents. The active agent can be associated, affixed, adhered, complexed, or otherwise physically or chemically bound to the surface of the particle. The active agents can be a small molecule (for example, less than 1000 daltons) or macromolecules (for example, equal to or greater than 1000 daltons); and the agents can be from biological sources or can be synthetically prepared or optionally the agents can be from biological sources that have subsequently been modified synthetically (e.g., semi-synthetic). The microparticles can be prepared with the agent, such as the bioactive agent, encapsulated in, associated with, or otherwise attached (e.g., covalently, non-covalently, ionically) to the surface of the particles in some manner. For example, the bioactive agent can be covalently bound to the particle, wherein the covalent bond is cleaved in vivo to release the active agent or the bioactive agent may remain covalently bound to the particles in vivo. Alternatively, the bioactive agent may be bound to the particle through electrostatic interactions, hydrogen bonding, hydrophobic interactions, or through the use of binding pairs, such as strepavidin/avidin and biotin. Alternatively, the microparticle composition may contain no active agent and thus is used as a placebo.

Bioactive agents include biologically, physiologically, or pharmacologically active substances that act locally or systemically in the human or animal body and include therapeutic, prophylactic, and/or diagnostic agents. Various forms of the medicaments or biologically active materials can be used, which are capable of being released from the solid matrix into adjacent tissues or fluids. A liquid or solid bioactive agent can be incorporated in the delivery systems described herein. The bioactive agents are typically at least very slightly water soluble, in one aspect moderately water soluble, and are diffusible through the polymeric composition. They can be acidic, basic, or amphoteric salts. The active agent can be administered as the free acid or base or as a pharmaceutically acceptable salt. The bioactive agent can be included in the compositions in the form of, for example, an uncharged molecule, a molecular complex, a salt, an ether, an ester, an amide, polymer-drug conjugate, or other form to provide the effective biological or physiological activity.

Examples of bioactive agents that can be incorporated into systems herein include, but are not limited to, peptides, proteins such as hormones, enzymes, antibodies and the like, nucleic acids such as aptamers, iRNA, siRNA, DNA, RNA, antisense nucleic acid or the like, antisense nucleic acid analogs or the like, low-molecular weight compounds, or high-molecular-weight compounds. Bioactive agents contemplated for use in the microparticle compositions include anabolic agents, antacids, anti-asthmatic agents, analeptic agents, anti-cholesterolemic and anti-lipid and antihyperlipidemic agents, anticholinergic agents, anti-coagulants, anti-convulsants, antidiabetic agents; anti-diarrheals, anti-edema agents; anti-emetics, antihelminthic agents; anti-infective agents including antibacterial and antimicrobial agents, anti-inflammatory agents, anti-manic agents, antimetabolite agents, anti-migraine agents; anti-nauseants, anti-neoplastic agents, anti-obesity agents and anorexic agents; antipruritic agents; anti-pyretic and analgesic agents, anti-smoking (smoking cessation) agents and anti-alcohol agents; anti-spasmodic agents, anti-thrombotic agents, antitubercular agents; anti-tussive agents, anti-uricemic agents, anti-anginal agents, antihistamines, anxiolytic agents; appetite suppressants and anorexic agents; attention deficit disorder and attention deficit hyperactivity disorder drugs; biologicals, cerebral dilators, coronary dilators, bronchiodilators, cytotoxic agents, decongestants, diuretics, diagnostic agents, erythropoietic agents, expectorants, gastrointestinal sedatives, central nervous system ("CNS") agents, CNS stimulants, hyperglycemic agents, hypnotics, hypoglycemic agents, immunomodulating agents, immunosuppressive agents, muscle relaxants, nicotine, parasympatholytics; sialagogues, ion-exchange resins, laxatives, mineral supplements, mucolytic agents, neuromuscular drugs, vasodialators, peripheral vasodilators, beta-agonists; tocolytic agents; psychotropics, psychostimulants, sedatives, stimulants, thyroid and anti-thyroid agents, tissue growth agents, uterine relaxants, vitamins, or antigenic materials.

Representative classes of drugs or bioactive agents that can be used in the microparticle composition include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, steroids, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, anti-alzheimers agents, antihypertensive agents, beta-adrenergic blocking agents, alpha-adrenergic blocking agents, nutritional agents, and the benzophenanthridine alkaloids. The bioactive agent can further be a substance capable of acting as a stimulant, sedative, hypnotic, analgesic, anticonvulsant.

Suitable diagnostic agents include any variety of medical imaging and diagnostic agents including, for example, MRI-based imaging such as iron oxide particles (including, for example superparamagnetic iron oxide, or SPIO, particles) and gadolinium-containing agents, among others. The microparticle compositions can also be prepared containing any of a variety of other dyes, contrast agents, fluorescent markers, imaging agents, and radiologic agents used in any variety of medical diagnostic and imaging technologies.

Depending on the application, the microparticle compositions can contain one or more active agents having a concentration from about 0 to 99.9 weight percent (wt. %) of the microparticle composition. In one aspect, the microparticle is a placebo with no bioactive agent. In another aspect, microparticle compositions intended for the delivery of vaccine antigens are generally only required to deliver very small or trace quantities of the bioactive agent (in this case, the vaccine antigen). Loading levels of the antigen in such cases can be less than 1 wt % in the final composition in some instances or can, in many instances, be below 0.1 wt %. In other aspects, the loading of the bioactive agent(s) can be higher, for example, from about 1 to about 90 wt %, preferably from about 1 to about 50 wt %, more preferably from about 1 to about 10%.

For the incorporation of bioactive peptides into the compositions, the bioactive peptide can be present in the microparticle composition at levels from about 1 to about 10 wt %. In other examples, a bioactive peptide with all of its associated soluble salts can be present in the microparticle composition at loading levels of about 40 wt % or higher. The percent loading is dependent on many factors including, but not limited to, the particular application, the choice and attributes of the agent itself, and the size and structure of the microparticle composition.

D. Excipients, Carriers, and Additives

The microparticle composition may further contain one or more pharmaceutically acceptable excipients, carriers, and additives. As used herein, the "carrier" is all components present in the pharmaceutical formulation other than the active ingredient or ingredients. The term "carrier" includes, but is not limited to, solvents, suspending agents, dispersants, buffers, pH modifying agents, isotonicity modifying agents, preservatives, antimicrobial agents, and combinations thereof.

Other additives include those useful for processing or preparation of the microparticle composition, can aid in the incorporation or stability of the bioactive agent, or can be useful in modifying performance of the microparticle composition, including, for example, modifying the rate of drug release, drug stability, water uptake, polymer degradation, among others.

The microparticle composition can contain other excipients including any number of other medically or pharmaceutically acceptable excipients such as preservatives, lipids, fatty acids, waxes, surfactants, plasticizers, porosigens, antioxidants, bulking agents, buffering agents, chelating agents, cosolvents, water-soluble agents, insoluble agents, metal cations, anions, salts, osmotic agents, synthetic polymers, biological polymers, hydrophilic polymers, polysaccharides, sugars, hydrophobic polymers, hydrophilic block copolymers, hydrophobic block copolymers, block copolymers containing hydrophilic and hydrophobic blocks. Such excipients can be used singly or in combinations of two or more excipients when preparing microparticle compositions. These excipients can be useful in order to alter or affect drug release, water uptake, polymer degradation, stability of the bioactive agent, among other properties.

The one or more excipients can be incorporated during preparation of the polymer admixture. In other aspects, these excipients can be added separately into the polymer solution itself. In still further aspects, these excipients can be incorporated into a first solution containing the bioactive agent dissolved or dispersed into a first solvent. In still further aspects, the excipients can be added into the polymer solution before, during, or after the bioactive agent is added into the polymer solution. In one aspect, such excipients can be used in the preparation of microparticle compositions that contain no bioactive agent. In another aspect, such excipients can be added directly into the polymer solution, alternatively, the excipients can first be dissolved or dispersed in a solvent which is then added into the polymer solution.

Examples of water soluble and hydrophilic excipients include poly(vinyl pyrrolidone) or PVP and copolymers containing one or more blocks of PVP along with blocks of other biocompatible polymers (for example, poly(lactide) or poly(lactide-co-glycolide) or polycaprolactone); poly(ethylene glycol) or PEG and copolymers containing blocks of PEG along with blocks of other biocompatible polymers (for example, poly(lactide) or poly(lactide-co-glycolide) or polycaprolactone); poly(ethylene oxide) or PEO, and copolymers containing one or more blocks of PEO along with blocks of other biocompatible polymers (for example, poly(lactide) or poly(lactide-co-glycolide) or polycaprolactone) as well as block copolymers containing PEO and poly(propylene oxide) or PPO such as the triblock copolymers of PEO-PPO-PEO (such as Poloxamers™, Pluronics™); and, modified copolymers of PPO and PEO containing ethylene diamine (Poloxamines™ and Tetronics™). In other aspects, the microparticle composition can be prepared containing one or more bioactive agents or one or more excipients or combinations thereof.

The one or more excipients can be incorporated into the microparticle composition at a concentration from about 1% to about 90% by weight of the composition. It is possible that a microparticle composition can be prepared that contains very little polymer. An example of such a situation can include a superparamagnetic iron oxide (SPIO) particle that is coated or encapsulated with small layer of a polymer composition using an emulsion or a spray drying or a fluid-bed processing technique included herein. Another example would include a core particle that is simply coated with a layer or layers of polymers including the polymeric microparticle composition by an appropriate coating technique (including, for example, an emulsion process or spray-coating or fluid-bed). In examples such as these, the microparticle composition can be largely comprised of either the SPIO particles or the core particle that has been encapsulated or coated with only a very small amount of polymer. In these and related applications, therefore, it is possible that the microparticle composition can contain greater than 80% or 90% or 99% of the excipient and, correspondingly, will contain very little of the polymeric composition.

E. Controlled Release Formulations

Microparticle compositions containing a bioactive agent can be used for pharmaceutical (e.g., drug delivery) applications as an injectable, long-acting (or modified release) drug-delivery formulation. Injectable microparticle compositions designed for drug-delivery purposes can release their bioactive agent over at a variety of different rates including release at a constant rate (zero-order rate of release), at a nearly constant rate (near zero-order or pseudo-zero-order), at a declining rate (first-order) and combinations thereof. The use of microparticles for the controlled release of bioactive agents and other substances can be used for the delivery of bioactive agents to specific sites, the precise control of release rates, or for the prolonged delivery of the bioactive agent for extended periods of time following the administration of the dosage form.

Advantages of delivering drugs by the injection of drug-loaded microparticles can include: sustained delivery of drugs at a therapeutic level; targeting to specific tissues or cells to increase potency and reduce potential harmful side effects; reducing the drug dose; decreasing the frequency of drug administration; potentially improving patient compliance; and, enabling the delivery of certain types of drugs, including those that are unstable and have short half-lives. In the case of drugs and other substances that are delivered by microparticles, realization of these benefits must be weighed against other factors on a case-by-case basis. For example, the polymers or matrix-forming materials used to prepare the microparticles, and from which the drugs are released, must be biocompatible and also compatible with the drug. In a further aspect, the polymer or matrix forming material can be biodegradable or absorbable by the subject. These materials must also be able to control the rate of release of the agent to be delivered, prevent any undesirable release (for example, rapid elution of a drug), and be available and converted into products at competitive cost. Moreover, delivery of these microparticle-based devices should not cause unnecessary patient discomfort upon administration, and it should be possible to deliver these microparticles precisely and to any desired location within the body.

Bioactive agents can be complexed or otherwise associated with other excipients contained in the microparticle composition that alter or enhance the biological effect, biological activity, stability, or release of the bioactive agent. An example includes a protein (for example, human growth hormone) that is complexed with a cation (for example the divalent cation of zinc ($Zn+2$) to improve the stability of the protein. In another aspect, these agents can simply be incorporated into the microparticle composition along with the bioactive agent without otherwise forming a complex or association between the bioactive agent and the other agent. Bioactive agents in the form of prodrugs, including polymeric prodrugs, can be incorporated into the microparticle compositions. Further aspects include the incorporation of bioactive agents that have been otherwise chemically modified, for example, for purposes of achieving biological targeting or for other means of affecting the pharmacokinetics or biodistribution of the native bioactive agent or any combinations of the above.

III. Methods of Making Microparticle Compositions

A. Microparticles

The microparticle compositions described herein can be prepared by a variety of methods known in the art including spray-drying; fluid-bed techniques; techniques that utilize spraying of solutions through nozzles (or jets) either into air or into liquids in order to prepare microparticles; cryogenic spray techniques (See U.S. Pat. No. 5,989,463, for example); ultrasonic spraying through nozzles (or jets) without or with the presence of applied electrical potential (e.g., electrostatic spraying) as described in U.S. Pat. No. 6,669,961; supercritical fluid techniques for the preparation of microparticle compositions; or any of the general techniques involving polymer precipitation or phase separation or coacervation and any combinations therein.

The following are representative methods for forming microparticles.

Spray Drying

In spray drying, the core material to be encapsulated is dispersed or dissolved in a solution. Typically, the solution is aqueous and preferably the solution includes a polymer. The solution or dispersion is pumped through a micronizing nozzle driven by a flow of compressed gas, and the resulting aerosol is suspended in a heated cyclone of air, allowing the solvent to evaporate from the microdroplets. The solidified microparticles pass into a second chamber and are trapped in a collection flask.

Interfacial Polycondensation

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

Hot Melt Encapsulation

In hot melt microencapsulation, the core material (to be encapsulated) is added to molten polymer. This mixture is suspended as molten droplets in a nonsolvent for the polymer (often oil-based) which has been heated to approximately 10° C. above the melting point of the polymer. The emulsion is maintained through vigorous stirring while the nonsolvent bath is quickly cooled below the glass transition of the polymer, causing the molten droplets to solidify and entrap the core material.

Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble drug particles in a polymeric solution for a period of time ranging from 0.5 hours to several months.

The stabilization of insoluble drug particles within the polymeric solution could be critical during scale-up. By stabilizing suspended drug particles within the dispersed phase, said particles can remain homogeneously dispersed throughout the polymeric solution as well as the resulting polymer matrix that forms during the process of microencapsulation. The homogeneous distribution of drug particles can be achieved in any kind of device, including microparticles, nanoparticles, rods, films, and other device.

Solvent evaporation microencapsulation (SEM) has several advantages. SEM allows for the determination of the best polymer-solvent-insoluble particle mixture that will aid in the formation of a homogeneous suspension that can be used to encapsulate the particles. SEM stabilizes the insoluble particles or within the polymeric solution, which will help during scale-up because one will be able to let suspensions of insoluble particles sit for long periods of time, making the process less time-dependent and less labor intensive. SEM allows for the encapsulated particles to remain suspended within a polymeric solution for up to 30 days, which may increase the amount of insoluble material entrapped within the polymeric matrix, potentially improving the physical properties of the drug delivery vehicle. SEM allows for the creation of microparticles or nanoparticles that have a more optimized release of the encapsulated material. For example, if the insoluble particle is localized to the surface of the microparticle or nanoparticle, the system will have a large 'burst' effect. In contrast, creating a homogeneous dispersion of the insoluble particle within the polymeric matrix will help to create a system with release kinetics that begin to approach the classical 'zero-ordered' release kinetics that are often perceived as being ideal in the field of drug delivery).

In one embodiment, the microparticles are prepared using an emulsion-based methodology. Examples include emulsion-solvent extraction methods (for example, U.S. Pat. Nos. 5,407,609; 5,650,173; 6,537,586; 6,540,393; 5,654,008), emulsion-solvent evaporation methods (for example, U.S. Pat. No. 4,530,840), or combinations of extraction and evaporation techniques (for example, U.S. Pat. No. 6,440,493). In these methods of preparing microparticle compositions, a polymer solution is typically prepared by dissolving the polymer or admixture of two or more polymers in a suitable solvent. The solvent can be a single solvent or a cosolvent. Generally speaking, a single solvent or an admixture of two or more solvents is referred to as a "solvent system."

The active agent is typically added to the polymer solution, either as a solid or as a solution or suspension. The active agent may or may not be soluble in the polymer solution. In some embodiments, the bioactive agent can be added after first dissolving or suspending the bioactive agent in a solvent system (the "first solvent") then adding this solution or suspension into the polymer solution. The bioactive agent can be dissolved in the first solvent and, upon adding this solution to the polymer solution, the bioactive agent can remain dissolved in the resulting polymer solution. Alternatively, the addition of the solution containing the bioactive agent to the polymer solution can result in the bioactive agent precipitating out of solution to a greater or lesser extent, depending on the overall solubility of the bioactive agent in the resulting solution.

The first solvent (i.e., the solvent system used to dissolve or suspend the bioactive agent) can be fully soluble in the polymer solution. In another aspect, the first solvent can be only partially soluble (or miscible) in the resulting polymer solution and a liquid-liquid emulsion is formed. In still another aspect, the first solvent can be only slightly soluble in the polymer solution; alternatively, the solvent can be nearly or virtually insoluble in the polymer solution. In situations when the first solvent is not fully soluble in the polymer solution, then a liquid-liquid emulsion will form. This emulsion can be either an oil-in-water emulsion or a water-in-oil emulsion depending on the particular solvent systems used to prepare the polymer and drug solutions. Preparing polymer solutions in the form of an emulsion is not uncommon and is often described as the "double-emulsion" technique for preparing microparticle compositions.

The bioactive agent can be distributed homogeneously through out the microparticle. Alternatively, the bioactive agent can be distributed heterogeneously in the microparticle matrix, i.e. encapsulated within (e.g., in the interior) of the microparticle or the exterior regions of the microparticle.

Solvent Removal Microencapsulation

In solvent removal microencapsulation, the polymer is typically dissolved in an oil miscible organic solvent and the bioactive agent to be encapsulated is added to the polymer solution as a suspension, dissolved in water, or as a solution in and organic solvent. Surface active agents can be added to improve the dispersion of the material to be encapsulated. An emulsion is formed by adding this suspension or solution to an oil with stirring, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

Phase Inversion. Nanoencapsulation ("PIN")

A preferred process is PIN. In PIN, a polymer is dissolved in an effective amount of a solvent. The agent to be encapsulated is also dissolved or dispersed in the effective amount of the solvent. The polymer, the agent and the solvent together form a mixture having a continuous phase, wherein the solvent is the continuous phase. The mixture is introduced into an effective amount of a nonsolvent to cause the spontaneous formation of the microencapsulated product, wherein the solvent and the nonsolvent are miscible. PIN has been described by Mathiowitz et al. in U.S. Pat. Nos. 6,131,211 and 6,235,224. A hydrophobic agent is dissolved in an effective amount of a first solvent that is free of polymer. The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less.

Melt-Solvent Evaporation Method

In the melt-solvent evaporation method, the polymer is heated to a point of sufficient fluidity to allow ease of manipulation (for example, stirring with a spatula). The temperature required to do this is dependent on the intrinsic properties of the polymer. For example, for crystalline polymers, the temperature will be above the melting point of the polymer. After reaching the desired temperature, the agent is added to the molten polymer and physically mixed while maintaining the temperature. The molten polymer and agent are mixed until the mixture reaches the maximum level of homogeneity for that particular system. The mixture is allowed to cool to room temperature and harden. This may result in melting of the agent in the polymer and/or dispersion of the agent in the polymer. This can result in an increase in solubility of the drug when the mixture is dissolved in organic solvent. The process is easy to scale up since it occurs prior to encapsulation. High shear turbines may be used to stir the dispersion, complemented by gradual addition of the agent into the polymer solution until the desired high loading is achieved. Alternatively the density of the polymer solution may be adjusted to prevent agent settling during stirring.

This method increases microparticle loading as well as uniformity of the resulting microparticles and of the agent within the microparticles. When an agent is formed into microspheres by double-emulsion solvent evaporation, transfer of the agent from the inner phase to the outer water phase can be prevented. This makes it possible to increase the percentage of agent entrapped within the microspheres, resulting in an increased amount of the drug in the microspheres.

The distribution of the agent in particles can also be made more uniform. This can improve the release kinetics of the agent. Generally, the agent is dissolved or dispersed together with a substance that has a high molecular weight in an organic solvent composition; with or without non-ionic surfactants of various hydrophilic-lipophilic ratios. The composition is introduced into an aqueous solution that contains a surfactant like PVA. The water-insoluble solvent forms an oil phase (inner phase) and is stirred into the aqueous solution as a water phase (outer phase). The O/W emulsion is combined with fresh water that contains PVA and is stirred to help aid the solvent evaporation. The aqueous solution contains an activator such as polyvinyl alcohol, whereby the oil phase is enclosed as small droplets within the aqueous solution as shells.

The microparticle can also be in the form of a multilayer microparticle. Multilayer microparticles can be prepared using any multiple steps or combination of steps of the techniques described above. This can include the preparation of a "core" particle by methods known in the art (including, for example, extrusion-spheronization or other granulation processes) that are then further processed in order to add one or more polymer layers to the core. For example, a first particle (a "core" particle) can be prepared by an emulsion-based method and treated using a second process such as a fluid-bed process in order to incorporate a second layer of material on the outside of the core particle. Alternatively, the multilayer microparticles can be prepared using processes that produce multiple layer particles directly (i.e., without the need for additional steps). Exemplary processes includes multiple or dual nozzle (or jet) configurations (otherwise termed nozzle-in-nozzle or dual nozzle configurations) for the preparation of multi-layer particles (for example, U.S. Pat. No. 6,669,961).

The polymer used to prepare the microparticle compositions can be a single polymer or can be a mixture of two or more polymers that are admixed together before preparing the microparticles. In one aspect, preparing the admixture of polymers can simply involve weighing out the appropriate quantities of the selected polymers and then using these individual materials to prepare a solution that is then used to prepare the microparticle composition. In another aspect, polymer solutions can be prepared separately using different polymers; then these polymer solutions can be combined prior to making the microparticle composition. In another aspect, the admixture of polymers can involve first combining and blending the various individual polymers in order to make a blend of the dry polymer solids; then that blend can be used to prepare the polymer solution that is used in the making of the microparticle composition. In still another aspect, the polymer admixture can be prepared by dissolving or dispersing the individual polymers in a solvent which is then evaporated leaving behind an admixture from a solvent-casting and evaporation process. In another aspect, the polymer admixture can be prepared by dissolving the individual polymers in a suitable solvent and then freezing and lyophilizing the sample to remove the solvent. In still another aspect, the polymer admixture can be prepared from the various individual polymers by supercritical fluid techniques.

The admixture of polymers can be prepared in the absence of a bioactive agent. In another aspect, the polymer admixture can be prepared with some or the entire amount of the bioactive agent that is used in the preparation of the microparticle composition.

Methods for Determining Particle Size

The mean particle diameter is the average diameter over the whole distribution. There are different types of means that can be calculated from the same set of particle size distribution data. For example, if there are ten spheres of diameters ranging from 1 to 10, the sum of their diameters from the distribution can be represented by ten spheres each of diameter 5.5; but the sum of their volumes has to be represented by ten spheres each having a diameter of 6.72. Each particle characterization technology will "see" the same sample differently. In the language of statistics, different technologies see particles through different "weighting factors." For example, when using tunneling electron microscopy (TEM), particles are measured on the basis of their number, but when using laser diffraction, the light scattering intensity of particles is detected on the basis of their volume. Different mean values thus have to be defined and used.

$D_{p,q}$ is the arithmetic mean for a given method of measuring particle size (p and q are restricted to integer values). If one uses an electron microscope to measure particles, one will measure the diameters with a reticule, add them up and divide the sum by the number of particles to get an average result. This is designated $D_{1,0}$, i.e., the number average. If one uses an image analysis the area of particles is what is most important. $D_{2,0}$ will be generated from the image analysis by adding all projected areas and dividing the sum by the total number of particles analyzed. Likewise, in a Coulter Principle measurement, one would get D3,0, and in a laser scattering experiment, one would get $D_{4,3}$. Even for a very simple system, the difference in the Dp,q, values can be significant. The difference between a number-averaged mean (q=0) and a mass-averaged mean (q=3) resides in the fact that in the number average the mean value represents values from particles with the largest population while in the mass average the mean value represents values from particles with the largest size. Therefore, for a real distribution, number distribution may be completely different from its corresponding mass distribution.

The microparticle compositions include particles having a diameter from about 10 nm to about 1000 microns. In general, the microparticle compositions can be prepared within this size range that are of a suitable size, or range of sizes, for use in any variety of medical, surgical, clinical, cosmetic, medical device, pharmaceutical and/or drug-delivery applications. In one aspect, the microparticles have a size in the range of from about 250 to about 1000 microns. In another aspect, the microparticles have a size in the range of from about 100 to about 250 microns. In another aspect, as in the case of microparticle compositions typically used for subcutaneous (SC) or intramuscular (IM) administration, the microparticles have a diameter in the range from about 20 to about 150 microns. In some embodiment, the microparticles have a diameter in the range from about 20 to about 50 microns, preferably from about 20 to about 40 microns. In other embodiment, the microparticles have a diameter in the range from about 1 to about 30 microns, preferably from about 1 to about 20 microns, more preferably from about 1 to about 10 microns. In one embodiment, microparticles are less than about 10 microns in size. In still another aspect, the microparticles are less than 1 micron in size. Further aspects include microparticles in the range of about 500-1000 nanometers (nm) or priority in the range of 200-500 nm. Still further aspects can include particles with sizes largely in the range of 100-200 nm and still further aspects include particles with size range of 10-100 nm.

In one embodiment, the mean particle size is from about 50 to about 100 microns, more preferably from about 50 to about 80 microns, most preferably from about 55 to about 75 microns. The particle size at the $90^{th}$ percentile of the particle size distribution, otherwise noted as either D(90) or $D_{90}$, is from about 80 microns to about 200 microns, preferably from about 80 microns to about 160 microns, more preferably from about 85 to about 155 microns. In other embodiments, the $D_{90}$ can be less than 80 microns, for examples, between about 30 and 50 microns, preferably between about 30 and 40 microns.

The size distribution of the particles (e.g., the variation from the mean) can be defined in a variety of ways, for example, as the ratio of $D_{90}$ (90% of the particles are smaller than this value) to $D_{10}$ (10% of the particles are smaller than this value). In one embodiment, $D_{90}/D_{10}$ is from about 2 to about 10, preferably from about 2 to about 6, more preferably from to about 5, most preferably from about 2.5 to about 4.8. In specific embodiments, the $D_{90}/D_{10}$ ratio is 2.5, 3.1, 3.4, or 4.8. Alternatively, the size distribution can be expressed by other means, including but not limited to, twice the mean.

Further, microparticles having different diameters can be blended together. In these instances, the formulations that are blended together can be the same composition of polymer or bioactive agent or excipient (or combinations therein) or different compositions. As an example, a microparticle formulation of one composition that has a particle size that is largely in the range of about 1-5 microns can be blended or mixed in any ratio (for example a 50% ratio by weight) with a microparticle formulation of the same or of a different composition that has a particle size that is largely in the range of about 100-250 nm. This admixture of the two microparticle formulations can then be prepared into a suitable suspension and administered for its intended purpose.

Nano- or Microtextured Surfaces

Microparticles prepared from blends of polylactide and polycaprolactone (e.g., 95:5, 90:10, and 80:20 blends of polylactide and polycaprolactone) and polylactide/polycaprolactone/polylactide-co-glycolide blends (e.g., 90% 75:25 PLG, 7.5% PL, and 2.5% PCL) made by the emulsion-based procedures described above exhibited nanotextured surfaces that were characterized by atomic force microscopy (AFM). Microparticles prepared from these blends exhibited nanotexturing or dimpling on the surface of the particles. In one embodiment, the particles contain dimples having diameters from about 10 to about 900 nanometers, preferably from about 10 to about 600 nm, more preferably from about 10 to about 5000 nm, more preferably from about 10 to about 250 nm, most preferably from about 10 to about 100 nm and/or nanotexturing on the surface. If the surface is nanotextured, the percent of the surface textured in one embodiment is at least 0.5%, preferably at least 1.0%, more preferably 2.5%, most preferably at least 5%. In another embodiment, the percent of the surface that is textured is from about 0.5% to about 30%, preferably from about 0.5% to about 20%, more preferably from about 0.5% to about 15%, and most preferably from about 0.5% to about 10%. In one embodiment, the particles have substantially uniform dimpling and/or texturing. In another embodiment, the microparticles are formed from copolymers comprising lactide and caprolactone.

This nanotexturing was not observed in microparticles prepared from homogeneous polymer blends. Thus, it is hypothesized that such dimpling occurs as a result of immiscible polymer blends which phase separate into identifiable domains during microparticles formation. For example, Raman spectroscopy of particles prepared from blends showed discrete domains of polycaprolactone in the surface of the particle. Without being bound by any theory, it is possible that these domains are nanoparticles embedded in the surface of the particle and/or protrude from the surface of the particle. Microparticles formed of polyhydroxyalkanoates such as P4HB and P4HB-3HB did not display areas of dimpling or other nanotexture.

Microparticles composed of two or more miscible (homogeneous) components showed homogeneous monotone phase-contrast images with little contrast or variation across the surface. In contrast, microparticles with immiscible (heterogeneous) components showed some contrast or variation in the phase-contrast images, representing the individual components across the surface of the microparticle. It is hypothesized that the nanotexturing or "dimpling" cause the particles to rotate when suspended in an injection vehicles. This rotation may prevent the particles from agglomerating and/or provide faster flow, thus resulting in improved injectability.

C. Mixtures

As demonstrated by the examples, microparticles which do not exhibit desirable flow patterns can be mixed with microparticles that do, in a wide range of concentrations. Combining formulations described herein into microparticle blends with standard microparticles compositions can improve the injectability of the standard microparticle composition. Blends or admixtures containing 5% or more, 10% or more, 20% or more, and 40% or more of the microparticles compositions described herein can be blended with a standard microparticle compositions. Examples 9 and 16 below describe microparticle compositions containing 25% of a 95:5 PL:PCL blend and 25% of a TephElast microparticle composition in combination with standard microparticle compositions. Addition of the PL:PCL blend and the TephElast composition improved the injectability of the formulations.

D. Coatings

Medical articles can be coated at least partially on the outside of the article with the microparticles compositions, to provide better surface properties. The article has improved flow properties over the surface, providing a smooth flow of liquid over its surface. The coating may include a first biocompatible polymer comprising (1) a blend of poly(DL-lactide) and polycaprolactone; (2) a copolymer of DL- or L-lactide and caprolactone; (3) a copolymer of DL-lactide, glycolide, and caprolactone; (4) poly(4-hydroxybutyrate-co-3-hydroxybutyrate); (5) a blend of any one or more of the first biocompatible polymers or (6) a blend of any one or more of the first biocompatible polymers with one or more additional biocompatible polymers, wherein the first and the one or more additional biocompatible polymers are different from each other. In one embodiment, the coating further contains a bioactive agent, which may be released in a controlled manner (e.g., delayed release, sustained release, pulsatile release, or combinations thereof). Examples of articles that can be coated include, but are not limited to, medical implants and devices.

Exemplary devices include, but are not limited to, sutures, suture fasteners, meniscus repair devices, rivets, tacks, staples, screws (including interference screws), bone plates and bone plating systems, surgical mesh, repair patches, slings, cardiovascular patches, orthopedic pins (including bone filling augmentation material), heart valves and vascular grafts, adhesion barriers, stents, guided tissue repair/regeneration devices, articular cartilage repair devices, nerve guides, tendon repair devices, atrial septal defect repair devices, pericardial patches, bulking and filling agents, vein valves, bone marrow scaffolds, meniscus regeneration devices, ligament and tendon grafts, ocular cell implants, spinal fusion cages, skin substitutes, dural substitutes, bone graft substitutes, bone dowels, wound dressings, and hemostats.

IV. Method of Administration

The microparticle compositions described herein are generally administered by injection, for example a 16 to 31 gauge needle, depending on the application. The needle can be regular wall, thin wall, ultra thin wall, or extra thin wall. Alternatively, the absolute size of the needle can be so small as not to be a size typically used in the microparticle injection art. In various aspects, the microparticles can be injected with a very small ID needle, such as a 23, 24, 25, 26, 27, 28, 29, 30, or 31 gauge or smaller inner diameter needle. The compositions can also be administered through a larger diameter tube, catheter, trocar, infusion tubing, or endoscopy/arthroscopic tubes. Catheters generally have a diameter between about 0.03 inches and 0.5 inches (rated as 3 Fr to 30 Fr, where 3 Fr is approximately 1 mm). Devices with diameters up to about 0.75 inches can also be used.

In one embodiment, the microparticle composition is capable of successful injection through a 23, 24, or 25 gauge or smaller inner diameter needle at a mean particle size of at least 90 microns, preferably at least 120 microns, and a D(90) particle size of at least 110 microns at a microparticle concentration in the fluid of at least 10 wt. %, preferably at least 20 wt %, more preferably at least 30 wt %, even more preferably at least 40%, most preferably at least 50 wt %.

In another embodiment, the use of the particular polymers described herein allows for a higher solids concentration of microparticles for a given needle ID as compared to the solids concentration of a standard composition, where all other variables are held essentially constant. Specifically, microparticles prepared from the preferred polymers described herein achieve both a smaller needle ID and a higher solids loading for a successful injection, as compared to the reference polymers. To compare such an effect, the polymers can be compared to the same reference polymer or polymers, that is 75:25 poly(DL-lactide-co-glycolide), poly(DL-lactide), polycaprolactone, or poly(4-hydroxybutyrate).

In specific aspects, the first microparticle solids content is at least 5%, at least 10%, at least 15%, at least 20%, at least 25%, or more higher than the second microparticle solids content. In one embodiment, the microparticle formulations described herein can be blended with a microparticle formulation known in the art to improve the injectability of the prior art microparticle formulation. In specific aspects, the final composition can contain a solids content from about 5% to less than about 100% (by weight) of a microparticle formulation described herein with the remainder of the composition being one or more microparticle formulations. In additional aspects, the final composition can contain a solids content of 10% by weight, 25% by weight, 50% by weight, 75% by weight or 90% by weight of a microparticle composition described herein with the remainder being one or more microparticle formulations known in the art.

The microparticle compositions are typically administered in vivo. The actual injection techniques are known to one of skill in the art, although it can be with a needle having a higher gauge number or a higher solids loading as described herein. The administration can be to any subject, such as a human.

Suitable injection techniques include, but are not limited to, parenteral and surgical administration by injection, infusion, or delivery through any suitable surgical or medical device including all needles, which as defined above, includes needle like devices and tubes, such as, but not limited to, needles, surgical needles, hypodermic needles, infusion needles, catheters, trocars, cannulas, tubes, and tubing, referred to collectively herein as "needles." Routes of administration can include any relevant medical, clinical, surgical, procedural, and/or parenteral route of administration including, but not limited to, intravenous, intraarterial, intramuscular, intraperitoneal, subcutaneous, intradermal, infusion, subconjunctive, and intracatheter (e.g., aurologic delivery), as well as administration via external scopic techniques such as, for example, arthroscopic or endoscopic techniques.

The compositions can be administered to specific locations (e.g., local delivery) including intrathecal, intracardiac, intraosseous (bone marrow), stereotactic-guided delivery, infusion delivery, CNS delivery, stereo-tactically administered delivery, orthopaedic delivery (for example, delivery to joints, into bone and/or bone defects, cardiovascular, inter- and intra- and para-ocular (including intravitreal and scleral and retrobulbar and sub-tenons delivery), as well as delivery to any multitude of other sites, locations, organs, etc.

Delivery of the administered microparticle product can be performed for any multitude of purposes ranging from medical device applications to drug-delivery or pharmaceutical purposes. The present technology has widespread applicability across a wide range of applications, routes of administration, or methods of administration, none of which are intended to be limited by the examples outlined herein. In a specific aspect, the microparticle compositions provide an important advantage for those applications where it is critical that the smallest size needle be employed, such as ocular, spinal, CNS, or joint administration.

In one embodiment, the microparticle composition is in a liquid suspending medium, which is also called an injection vehicle or fluid or diluent prior to administration. These suspensions are typically heterogeneous systems containing the solid, essentially insoluble dispersed material (the microparticle composition) suspended or disbursed in a liquid phase (the injection vehicle). The injection vehicle is typically sterile, stable, and capable of being delivered through a needle without clogging or otherwise blocking the delivery of the microparticle suspension.

The injection vehicle or liquid phase can be aqueous or non-aqueous. The liquid medium should be medically, surgically, biologically, and/or pharmaceutically acceptable. The injection vehicle can be of relatively low or high viscosity but should be of sufficient viscosity so that the resulting suspension formed from the microparticle composition is of suitable viscosity to be passed through the desired needle. This limit can range depending on the type of needle or device being used to perform the administration, the length of the needle or device, the inside diameter of the needle, etc. Suitable aqueous injection vehicles include, but are not limited to, saline solution. Suitable nonaqueous injection vehicles include, but are not limited to, fluorinated liquid vehicles such as polyfluoroalkylmethylsiloxanes, Miglyol or other pharmaceutically acceptable oils and oil-based vehicles.

The injection vehicle may contain one or more viscosity-modifying agents and/or surfactants. Other suitable additives include, but are not limited to, buffers, osmotic agents, and preservatives. Examples of viscosity-modifying agents include, but are not limited to, synthetic polymers, such as poloxamers, Pluronics, or polyvinyl pyrrolidone; polysaccharides, such as sodium carboxymethyl cellulose (CMC); natural polymers, such as gelatin, hyaluronic acid, or collagen; and the like. The viscosity-modifying agent can be used in any concentration range that provides sufficient flow through the needle used for a particular application. As such, the injection vehicle can be a low viscosity solution with or without a surfactant; further, the injection vehicle can be a medium or high viscosity solution. Surfactants can range from being anionic, cationic, amphiphilic, or nonionic. Examples of surfactants include, but are not limited to, TWEEN® 20 (polysorbate 20), TWEEN® 80 (polysorbate 80), sodium dodecylsulfate, or sodium laurylsulfate.

Specific examples of injection vehicles include, but are not limited to, those that are identical or similar to those vehicles that are used in commercial pharmaceutical formulations. In various aspects, the injection vehicle contains carboxymethyl cellulose (CMC) as a viscosity-modifying agent in a concentration range of from about 0.05 wt % to about 25 wt %, preferably from 0.05 wt % to 3 wt %, more preferably from 3 wt % to 6 wt %, even more preferably from 6 wt % to 10 wt %, most preferably from 10 to 25 wt %. Still further, an injection vehicle can contain a surfactant, for example TWEEN® 20 or TWEEN® 80, in a concentration range of about 0.05 wt % to 0.5 wt %. Alternatively, an injection vehicle can be prepared using the viscosity modifying agent poloxamer (or Pluronics) in a concentration range of from 0.5 wt % to 50 wt %; 0.05 wt % to 5 wt %, 5 wt % to 20 wt %; or 20 wt % to 50 wt %. In one embodiment, the injection vehicle requires little or no surfactant. This may be due to the fact that the surface characteristics of the polymers are substitutes for the surfactant properties The injection vehicle can also contain polyvinylpyrrolidone (PVP) as a viscosity-modifying agent in the range of 0.1 wt % to 10 wt %. The injection vehicle can contain other additives such as osmotic agents that can be useful in making the osmolality of the suspension close to that of physiological environments. Another additive that can be used in the injection vehicle is mannitol; for example, injection vehicles can contain mannitol in the range of about 0.5 wt % to 15 wt %, 0.5 to 5 wt %, or 5 wt % to 15 wt %.

The microparticle compositions are typically dispersed or suspended in the injection vehicle. The concentration of microparticles dispersed or suspended in a particular volume of injection vehicle can range from dilute to concentrated. As used herein, the concentration of the microparticles refers to the solids loading of the microparticles in the liquid injection vehicle. The required concentration of solids in the suspension can be determined by the application or by the strength or activity of the bioactive agent or both. In one embodiment, the concentration of solids in the suspension is from about 0.1 wt % to about 75 wt %. Preferred solids contents include from about 0.1 wt % to about 1 wt %, from about 1 wt % to about 10 wt %, from about 5 wt % to about 50 wt %, or from about 50 wt % to about 75 wt %.

C. Sterilization

The microparticle compositions can be prepared aseptically and used without any further processing in order to have a sterile product suitable for administration to a subject. In other aspects, the microparticle composition can be prepared non-aseptically and then be subjected to a terminal sterilization operation in order to have a sterile product that is suitable for administration to a subject. Without intending to be limiting, terminal sterilization operations can include exposure to irradiation such as gamma-irradiation or electron-beam radiation, or exposure to ethylene oxide gas.

V. Methods of Use

The microparticles are delivered to a subject by injection through a needle, wherein the inner diameter of the needle is smaller than what would be expected to be useful, based on the diameter of the microparticles. The needle ID can be any size. By "successfully" injecting, it is meant a "pass" as recited in the examples, wherein the following criteria are met: (1) the complete contents of the test syringe were fully expelled out of syringe (i.e., the plunger was successfully fully depressed to the tip of the syringe), (2) no clogs or blockages occurred that stopped the flow of the suspension out of the needle in the syringe, (3) the contents were expressed from the syringe using a constant, steady finger pressure from start-to-finish, and (4) disassembly and inspection of the tip of the syringe and the needle showed no unusual build-up or accumulation of the microparticle material inside these components. A failure to successfully achieve any one of these criteria is a "failure." A pass occurs when 3 replicate samples are successfully expelled according to these criteria. A fail is recorded when any 1 or more of 3 replicate samples fail these criteria. Therefore, the grade of Passing required the highest standard of having all 3 replicates meet the specified criteria described here. As claimed, a successful injection into a subject is a single injection that would have been successful under these in vitro test criteria, had it been tested in vitro three times and passed all three times.

EXAMPLES

The present invention will be further understood by reference to the following non-limiting examples. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Preparation of Microparticle Formulations

Polymers Used in the Examples.

Microparticle formulations were prepared using a variety of biodegradable polyester polymers. The polymers used in these examples are identified below in Table 3. Individual polymers have been assigned a unique letter identifier code to allow simple reference to individual polymers in subsequent examples.

TABLE 3

Description of the polymers used in the examples

| Polymer Identifier Code | Polymer descriptions (copolymer ratios and composition)[(1)] | Reported polymer inherent viscosity[(2)] (dL/g) | Reported molecular weight by GPC ($M_w$) (Daltons) | Vendor[(3)] | Vendor lot number |
|---|---|---|---|---|---|
| A | 75:25 DL-PLG | 0.46 | | BPI | D98051 |
| B | DL-PL | 1.04 | | APT | APT080802-1 |
| C | Polycaprolactone, PCL | | 42,000 | Aldrich | 01222JD |
| D | TephaFLEX ® (low MW) | | 150,000 | Tepha | DC-10-2-1 |
| E | TephaFLEX ® (high MW) | | 400,000 | Tepha | DC-8-62-1 |
| F | TephELAST, 30% (high MW) | | 560,000 | Tepha | DC-06-9-1 |
| I | 72:25 DL-lactide/caprolactone | 0.11 | | Alkermes | 01-141-134 |
| O | TephELAST, 30% (low MW) | | 130,000 | Tepha | DC 06-91-1 |
| P | TephELAST, 20% (low MW) | | 130,000 | Tepha | DC-06-56-2 (low) |
| S | 70:24:06 DL-G-CPL 4E copolymer (ester(capped)end-group) | 0.41 | | Lakeshore | LX00111-71 |
| T | 38:38:24 DL-G-CPL 4E copolymer (ester(capped)end-group) | 0.39 | | Lakeshore | LX00111-70 |
| U | 67:08:25 DL-G-CPL 4E copolymer (ester(capped)end-group) | 0.41 | | Lakeshore | LX00111-83 |
| V | DL-PL (low viscosity) | 0.35 | | BPI | D01050 |
| W | 50:50 DL-PLG | 0.63 | | BPI | D01007 |
| X | 65:35 DL-PLG | 0.65 | | Alkermes | 1230-525 |
| Y | 75:25 DL-PLG, 6A (acid end-group) | 0.65 | | Alkermes | 00-141-100 |
| Z | TephELAST, 20% (high MW) | | 400,000 | Tepha | 225-031 |

NOTES:

(1)Poly(DL-lactide) and poly(DL-lactide-co-glycolide) copolymers have capped end-groups unless otherwise specified above as having acid end-groups. Otherwise, polymer descriptions and abbreviations are as follows:

| | |
|---|---|
| DL-PLG | Poly(DL-lactide-co-glycolide) prepared from the indicated mole ratios of DL-lactide and glycolide, respectively. |
| DL-PL | Poly(DL-lactide) |
| PCL | Polycaprolactone |
| DL-lactide/caprolactone | Random copolymers prepared from the indicated mole ratios of DL-lactide and caprolactone, respectively. |
| DL-G-CPL | Random copolymer prepared from the indicated mole ratios of DL lactide:glycolide:caprolactone |
| TEPHAFLEX ® | Poly(4-hydroxybutyrate), prepared synthetically or biologically |
| TEPHELAST ® | Poly(4-hydroxybutyrate-co-3-hydroxybutyrate) copolymer containing the indicated mole-percent of the 4-hydroxybutyrate monomer, with the balance of mole percent being 3-hydroxybutyrate prepared synthetically or biologically |

(2)Unless otherwise specified, the Inherent Viscosity (IV) was determined at 30° C. from solutions prepared at 0.5 g/dL in chloroform. One exception was polymer sample (W), a 50:50 DL-PLG, where the IV was measured at 30° C. from a 0.5 g/dL solution in hexafluoroisopropanol (HFIP)

TABLE 3-continued

| | |
|---|---|
| [(3)]Vendors or suppliers are identified as follows: | |
| BPI | Birmingham Polymers Inc. (Birmingham, AL) |
| APT | Absorbable Polymer Technologies (Birmingham, AL) |
| Aldrich | Aldrich Chemical Co. (Milwaukee, WI) |
| Tepha | Tepha, Inc. (Lexington, MA) |
| Lakeshore | Lakeshore Biomaterials (Birmingham, AL) |
| Alkermes | Alkermes, Inc. (Cambridge, MA) |

Other Materials

Methylene chloride (Fisherbrand Optima, ACS grade) and ethyl acetate (Fisherbrand, NF grade) was used as received from Fisher Scientific. Poly(vinyl alcohol), ultra pure grade, was purchased from Amresco (Solon, Ohio). The deionized water used in these studies was from an in-house deionization system (US Filter). Poly(vinyl alcohol) (PVA), ultra pure grade (87.5-89% hydrolysis) was purchased from Amresco (Solon, Ohio). Nalmefene hydrochloride was obtained from Mallinckrodt Inc. (St. Louis, Mo.) and converted to the free base by adjusting the pH of an aqueous solution of the hydrochloride salt to pH 7. The resulting free base was washed liberally with deionized water and was then frozen and lyophilized to obtain a dry powdered product. The reported melting point of the hydrochloride salt is 180-185° C. (Merck Index) and that of the free base is 188-190° C. (as per the Mallinckrodt MSDS). The measured melting point of the free base was 189.1° C. as determined by DSC on a TA Instruments DSC 2920 using a 10-15 mg sample at a scan rate of 10° C./minute. Goserelin acetate was obtained from Genzyme Corporation (Cambridge, Mass.) and then ground to a fine powder manually using a mortar and pestle.

Preparation of 2% Poly(Vinyl Alcohol) Aqueous Solution

A 2 wt % aqueous solution of PVA was prepared as follows. A container holding 5.9 kg deionized water was stirred vigorously at 650 rpm using a Stir-Pak heavy-duty (9-900 rpm) mixer and a 3" diameter impeller (Cole-Parmer). PVA was then slowly added (120 grams) to the stirred container. The mixture was heated to 90° C. at which time the heat-source was turned off. With continued stirring, the solution was allowed to cool until the temperature dropped below about 30° C. At this time, the solution was filtered through a 0.22 micron filter (Millipore Millipak 200).

Preparation of Dispersed Phase (DP) Processing Solutions.

Unless otherwise specified, all microparticle formulations were prepared from dispersed phase (DP) solutions consisting of a solution of 20 wt % polymer dissolved in methylene chloride. The 20% dispersed phase (DP) polymer solutions were prepared by transferring 10 grams of the specified polymer (or blend of polymers) to a 60-mL glass jar. To this container, was added 40 grams of methylene chloride. A magnetic stir-bar was added to the jar which was then securely closed with a screw-cap closure. The sample was stirred thoroughly until the polymer was completely dissolved. When specified, DP solutions were prepared in a similar manner using ethyl acetate instead of methylene chloride.

Alternative preparation of dispersed phase (DP) polymer solutions: 10% nalmefene base, 20% polymer concentration.

Microsphere formulations were made comprising nalmefene base using dispersed phase (DP) solutions prepared at a polymer concentration of 20 wt % in methylene chloride. These DP solutions were prepared by transferring 9 grams of the specified polymer (or blend of polymers) to a 60-mL glass jar. To this container, was added 36 grams of methylene chloride. Using a stir bar and a magnetic stir place, this solution was stirred until the polymer was completely dissolved. At this point, 1 gram of nalmefene base was added to the jar which was then stirred until the drug dissolved into solution. The nalmefene loading used to prepare these microparticle compositions was 10% based on the total combined weight of drug plus polymer in the DP solution.

Preparation of Continuous Phase (CP) Processing Solution.

All microsphere formulations were prepared using a continuous phase (CP) solution consisting of 2% PVA solution (described previously) that was saturated in methylene chloride. 500 grams of the filtered 2 wt % PVA solution was transferred to a 1-L glass jar. About 7 grams of methylene chloride was then added to the container. The container was securely closed and then stirred thoroughly with a magnetic stir bar and stir plate for at least 1 hour before starting to prepare the microparticle formulation.

Procedure for Making Microparticles

A Silverson L4R-T mixer with a laboratory in-line mixer head with a general-purpose disintegrating head (stator screen) was configured. Separately, the Dispersed Phase (DP) solution and the Continuous Phase (CP) solution were delivered into the inlet assembly of the mixer head. The DP and CP solutions were delivered into the mixer head at flow rates of 20 g/min and 125 g/min, respectively. A mixer stir speed was selected based on prior experience in order to make product having the desired particle size (mean of about 60 microns). This was important to ensure that the various microparticle formulations have similar particle size and particle size distributions in order to avoid results that are based on differences in particle size rather than the polymer compositions. Stir speeds used in this emulsification process can vary depending on processing and solution conditions but were typically in the range of 900-1300 rpm. The effluent emulsion from the mixer was then immediately diluted with additional water (the Extraction Phase or EP solution) at an emulsion:EP weight ratio of approximately 1:15. The resulting effluent was then collected in an 18-gallon tank that was equipped with a suitable mixer (Lightnin G3U05R or similar) and the resulting effluent was stirred at about 600-900 rpm. The DP and CP solutions were processed through the Silverson mixer until all the DP solution had been delivered. When finished, delivery of the DP, CP, and EP solutions was discontinued. The microparticle suspension was stirred in the tank overnight (approximately 18 hours). At this point, a peristaltic pump was used to pass the microparticle suspension across a set of 125 micron and 25 micron collection screens (Fisherbrand U.S. Standard stainless steel test sieves) to remove oversized and undersized particles, respectively. An additional 4-L of fresh deionized water was used to rinse the microparticle product that had been collected on top of the 25 micron collection screen. The product obtained between the 25 and 125 micron mesh screens was the material that is then used for subsequent evaluations.

The 25 micron collection screen containing the wet 25-125 micron microparticle formulation was placed under a laminar flow hood and allowed to dry completely (for example, overnight) under ambient conditions. Once dry, the 25425 micron microparticle product was removed from the screen using a stainless steel or Teflon spatula and was placed in a 20-mL scintillation vial which is kept securely closed and stored desiccated and frozen. In some cases, as indicated, the finished dry powder can be passed through a 212 or 300 micron test screen prior to injectability testing in order to remove any particle aggregates that can have formed during storage. It is important to note that the mesh size used in this dry-sieving operation was much larger than the 125 micron test sieve used during the preparation of the microparticle formulations, which ensures that this operation does not adversely affect the size of the microparticle composition in any other way than to remove oversized aggregates formed during storage.

Drug Content Analysis

Triplicate samples were prepared of nalmefene-containing formulations by accurately weighing about 20-30 mg of the microparticle formulation and dissolving this into about 2 mL of glacial acetic acid. This solution is then diluted to a total volume of 25 mL using phosphate-buffered saline (pH 7.4). This solution is filtered with a 0.45 micron syringe filter prior to analysis by HPLC. Nalmefene samples were analyzed using a Curo-Sil-PFP 5 micron 3.2×250 mm column (Phenomenex; Torrance, Calif.) at a flow rate of 1 mL/minute by a gradient method (comprising a mobile phase of 10 nM ammonium acetate buffer, pH 4, that is reduced over a 12-minute gradient from 100% to 35% using acetonitrile). Samples were analyzed at a wavelength of 268 nm using a standard curve ranging from 100 μg/mL to 5 μg/mL.

Goserelin samples were analyzed by an isocratic LC method using a mobile phase consisting of a 74:26 (v/v) ratio of 0.1% TFA in water and 0.1% TFA in acetonitrile, respectively. Chromatography was performed using a Luna C-18, 3-micron 4.6×140 mm column (Phenomenex; Torrance, Calif.) at a flow rate of 1 mL/minute. Samples were analyzed at a wavelength of 220 nm using a standard curve ranging from 100 μg/mL to 5 μg/mL.

Particle Size Analysis of a Microparticle Formulation.

Microparticle formulations were analyzed for particle size and particle size distribution using a Coulter LS-13,320 laser diffraction particle size analyzer with micro-volume module. Briefly, approximately 100 mg of a test sample was accurately weighed into a test tube. Then 4 mL aliquot of a 0.1 wt % TWEEN® 80 solution was added to the test tube which was then sonicated for approximately 15 seconds (Cole-Parmer sonicator batch Model 8893). After sonication, the sample was then mixed by vortex mixer (Vortex Genie; Fisher Scientific) at a setting of "high" for approximately 15 seconds. Portions of this sample were then added to the stirred sample cell of the particle size analyzer to get suitable signal. Size analysis was carried out using a Fraunhofer optical model and results were calculated using volume-average statistics. The reported results include the mean particle size (mean) and the particle size at the $90^{th}$-percentile of the particle size distribution, otherwise noted as either D(90) or $D_{90}$, which serves as an indicator of the size range on the upper end of the particle size distribution. The mean particle size and the particle size at the $90^{th}$ percentile for the microparticles prepared in Examples 3, 4, 6, and 7-21 are shown in Tables 3, 4, 6, and 7-21, respectively.

Injection Vehicle Composition and Preparation.

(a) Preparation of an injection vehicle consisting of 0.5 wt % sodium carboxymethyl cellulose (CMC) and 0.1 wt % TWEEN® 80.

Unless otherwise specified the injection vehicle used in these injectability screening studies and in the capillary viscosity testing of microparticle suspensions was carried out using an injection vehicle composed of 0.5 wt % sodium carboxymethylcellulose (CMC) and 0.1 wt % TWEEN® 80.

A 1-L batch of this injection vehicle was prepared as follows. 1 gram of TWEEN® 80 (Polysorbate 80, NF grade; Spectrum Chemicals; Gardena Calif.) was added into a 2-L beaker containing 996 grams of deionized water. The beaker was placed on a hot-plate and an external stir motor was used to stir the contents of the beaker at about 600 rpm. 5 grams of low-viscosity sodium carboxymethylcellulose (USP grade; Spectrum chemicals; Gardena, Calif.) were slowly dispersed into the stirred beaker. The container was heated to about 80-90° C., then heating was discontinued and the contents of the beaker allowed to cool while stirring. Once the solution reached room temperature, 12-mL aliquots of the solution were transferred into 20-cc serum vials and then the vials were crimped closed using septum and seals. The vials were autoclaved at 120° C. for 20 minutes (Yamato Sterilizer, Model SM-510; Yamato Scientific Co), labeled appropriately and then stored at room temperature.

The solution viscosity of this injection vehicle (consisting of 0.5 wt % sodium carboxymethyl cellulose (CMC), USP low viscosity grade and 0.1 wt % TWEEN® 80) was determined at 22° C. using a Brookfield viscometer, Model RVTD. Measurements were carried out using the small sample adapter with Spindle Size #21 and at a measurement speed setting of 100 rpm. The resulting viscosity measurement on the injection vehicle was 8.5 cps (22° C.).

Alternate injection vehicle composition: 0.5 wt % CMC and 0.25 wt % TWEEN® 80 was prepared as described above, with the exception that 2.5 grams of TWEEN® 80 (polysorbate 80) were used.

Alternate injection vehicle composition: 0.5 wt % CMC and 0.1 wt % sodium dodecylsufate (SDS). This was prepared as described above except the TWEEN® 80 was replaced with 1 gram of sodium dodecysulfate (electrophoresis grade; Fisher Scientific).

Injectability Testing and Test Criteria.

Becton Dickinson (BD) 1-mL BD LUER-LOK™ syringes (BD Product Number 309628) were used. Unless otherwise specified, Beckon-Dickinson BD PrecisionGlide needles of standard wall thickness were used as shown in Table 4.

TABLE 4

| Needle gauge and length | | |
|---|---|---|
| Gauge No. | Length | BD Product Number |
| 18 G | 1 inch | 305195 |
| 20 G | 1 inch | 305175 |
| 21 G | 1½ inch | 305165 |
| 23 G | 1 inch | 305145 |
| 25 G | ⅝ inch | 305122 |
| 27 G | ½ inch | 305109 |

Exceptions include the following needles (where specified):

(1) 26 G-TW (thin wall) needle, ⅝" length;

BD PrecisionGlide (Product number 305115)

(2) 25 G-UTW×1" (ultra thin wall) needle

TERUMO® brand, Terumo Medical Corporation (Elkton, Md.), Product Code NN-2525R

Triplicate samples of a microparticle formulation were prepared for syringability testing as follows. The plunger was removed from a 1-mL syringe (Syringe 1). A female-female luer-lock syringe connector was affixed to the tip of the syringe (Cole-Parmer catalog number EW-45500-22). The open end of the female-female connector was closed using a male luer-lock plug (Cole-Parmer catalog number EW-45503-56). Using an analytical balance, a predetermined amount of the microparticle formulation was weighed into the syringe based on the suspension concentration (percent solids) that was to be tested as shown in Table 5 below. For example, a sample being prepared for testing at a suspension concentration level of 30% solids would have 100 mg of a microparticle formulation weighed into Syringe 1.

TABLE 5

| Parameters of formulations to be tested | | |
|---|---|---|
| Percent solids to be tested | Amount of formulation weighed into Syringe 1 | Injection vehicle used in Syringe 2 |
| 10% | 100 mg | 0.9 cc |
| 20% | 100 mg | 0.4 cc |
| 30% | 100 mg | 0.2 cc |
| 40% | 200 mg | 0.3 cc |
| 50% | 200 mg | 0.2 cc |

The plunger was carefully introduced back into the barrel of the syringe. After loosening the male luer-lock plug slightly, the plunger was gently depressed towards the tip of the syringe in order to remove most of the void-space from inside the syringe barrel. The plunger was not pressed far enough to compress or compact the microparticle product into the tip of the syringe. The male luer-lock plug was then gently secured in the tip of Syringe 1 to prevent loss of the sample from the syringe prior to testing.

A second 1-mL syringe then was used to obtain the desired quantity of injection vehicle (Syringe 2). A 21-gauge needle was affixed to Syringe 2. The desired quantity of the injection vehicle was drawn up into the syringe. This quantity was based on the target concentration level (percent solids level) that was being analyzed as identified in Table 5. When the desired amount of injection vehicle had been placed into Syringe 2, then the needle was removed from Syringe 2.

The male luer-lock plug was removed from Syringe 1 and then Syringes 1 and 2 were securely connected tip-to-tip using the female-female connector. This manipulation was done carefully so as to prevent loss of microsphere material from Syringe 1 and injection vehicle from Syringe 2. The injection vehicle in Syringe 2 was then expressed into Syringe 1; the combined contents were then expelled back and forth between the two syringes by moving the plungers back and forth. The contents were mixed by approximately 20 transfers back and forth between the 2 syringes.

Immediately after mixing, the suspension was transferred to one syringe which was held in an upright orientation (tip pointed upwards) and was then disconnected from the female-female connector. The appropriate needle was then securely affixed to the syringe. Any extra air on the inside of the syringe was then carefully expelled out through the needle. At this point, the sample was ready for injectability testing. The sample syringe (with needle attached) was then inverted so that the needle was pointed down. The plunger was depressed at an equivalent rate of approximately 0.5 mL over 5 seconds using a constant, steady finger pressure by the operator.

The injectability of an individual syringe (or trial) was considered a "pass" if the complete content of the syringe was expelled without any clogs or blockages from occurring that prevented stopped the flow of the suspension out of the needle or if there was no noticeable change in pressure that interrupted the constant, steady depression of the plunger by the operator.

An individual trial was considered a "pass" only if all of the following criteria were met:

The complete contents of the test syringe were fully expelled out of syringe (i.e., the plunger was successfully fully depressed to the tip of the syringe)

No clogs or blockages occurred that stopped the flow of the suspension out of the needle in the syringe The contents were expressed from the syringe using a constant, steady finger pressure from start-to-finish Disassembly and inspection of the tip of the syringe and the needle showed no unusual build-up or accumulation of the microparticle material inside these components.

A failure to successfully achieve any one of these outcomes caused an individual trial to be labeled a "failure".

The "Injectability" of a microparticle formulation was evaluated at specific test conditions of: (a) suspension concentration levels and (b) needle diameter (or gauge).

Injectability testing was carried out at each set of test conditions using triplicate trials.

The injectability of a microparticle formulation at a particular set of test conditions was graded a "Pass" if all three replicate trials were graded as a "pass". In contrast, the injectability of a microparticle formulation at a particular set of test conditions was graded a "Fail" if any one of the three replicate trials was labeled a "failure" as described above.

Capillary Viscometry Testing of Concentrated Suspensions of Microparticle Formulations Suspended in Injection Vehicle Media.

In order to characterize the flow characteristics of concentrated microparticle suspensions through small-diameter orifices, capillary viscometry was utilized in order to compare the flow properties of various microparticle formulations.

Microparticle formulations were suspended in 0.1 wt % TWEEN® 80. Microparticle suspensions were prepared at a fixed concentration level of 40% solids (by weight) in the injection vehicle. 1 gram of a microparticle formulation was added to a 20-mL glass scintillation vial. To this vial, was added 5 mL of the injection vehicle. The vial was next mixed by vortexing for approximately 30 seconds. The resulting suspension was then poured into a Canon-Fenske #150 capillary viscometer tube. This tube was placed inside a constant-temperature bath (Canon Model CT-500) that was maintained at room temperature of 22° C. The tube was maintained in the bath for 10 minutes to allow temperature equilibration. At this time, the tube was briefly removed from the bath and shaken by hand to re-suspend the microparticle suspension, then the tube was replaced back inside the bath. Using a pipette bulb, the suspension was drawn up through the capillary (by vacuum pressure) until the suspension was drawn above the top line of the viscometer tube. Once the bulb was removed, the suspension begins to fall through the tube by gravity. Using a timer (stopwatch), the time required for the solution (suspension) to pass between the two marked lines of the capillary viscometer was measured. This time is the "fall time" (in seconds). The steps of removing the tube from the bath to shake the suspension and then replacing the tube in the bath and measuring the fall time of the suspension is repeated to get three replicate fall time measurements on the microparticle suspension. The mean and standard deviation of the three replicate fall time measurements are calculated. This procedure can also be performed on the injection vehicle itself in order to obtain the fall time of the vehicle itself. The fall time results serve as relative indicators of viscosity of the individual solutions or suspensions.

Example 2

Injectability Testing of Representative PRIOR ART Microparticle Formulations Prepared from Biodegradable Polyesters PLG, DL-PL, and PCL In this and subsequent Examples, information on the composition and characterization of individual microparticle batches are tabulated along with the results of injectability screening tests. Using Table 6 below as an example, information on individual microparticle batches is listed in columns. The first section of information for each sample identifies sample lot number, the polymer(s) used to prepare the sample, and also indicates whether a dry-sieving step was performed. The specific polymer (or polymers) used to prepare the individual microparticle sample are listed as component 1, 2, and 3. The letter code used in this table refers to specific polymers that are identified above. When multiple polymers have been combined in an admixture in the preparation of a microparticle composition, the weight percent of each polymer component used to prepare the admixture will also be identified in the table. Additionally, particle size results are included in this table to facilitate comparison between individual samples. Below this information, the table contains the results of the injectability screening evaluations that were conducted on individual microparticle batches.

Microparticle formulations were made from 75:25 poly(DL-lactide-co-glycolide), DL-PLG (Polymer A), poly(DL-lactide), DL-PL (Polymer B), and polycaprolactone, PCL (Polymer C) as described above. These PLG, DL-PL, and PCL microparticle formulations are identified by their individual lot numbers 0061-020, 0037-099, and 0037-162, respectively.

These microparticle formulations were evaluated for syringe injectability using the 0.1 wt % TWEEN® 80 (polysorbate 80) injection vehicle, as described above. These evaluations were carried out at a variety of microparticle suspension concentrations and using hypodermic needles of varying diameters (or Gauge number). Needles of increasing Gauge number are associated with needles having smaller overall outside diameters. Because of this, it is advantageous to be able to administer a particular microparticle suspension from syringes having the largest Gauge number (or smallest overall outside diameter).

TABLE 6

Batch information and injectability screening results of Example 2.

| Formulation Parameters Needle size (Gauge) | Suspension Conc., wt % | 75:25 DL-PLG formulation | DL-PL formulation | PCL formulation |
|---|---|---|---|---|
| Formulation lot number | | 0061-020 | 0037-099 | 0037-162 |
| Polymer component 1 | | 100% A | 100% B | 100% C |
| Polymer component 2 | | | | |
| Polymer component 3 | | | | |
| Dry sieve performed | | None | None | None |
| Mean particle size, microns | | 77.7 | 85.0 | 82.7 |
| D(90) particle size, microns | | 115.8 | 118.0 | 115.8 |
| 20G | 10% | | | |
| | 20% | Pass | Pass | Pass |
| | 30% | | | |
| | 40% | | | |
| | 50% | Pass | Pass | Pass |
| 21G | 10% | Pass | Pass | Pass |
| | 20% | Fail | Fail | Pass |
| | 30% | | | Fail |
| | 40% | | | |
| | 50% | | | |
| 23G | 10% | | | Fail |
| | 20% | | | Fail |
| | 30% | | | Fail |
| | 40% | | | |
| | 50% | | | |
| 25G | 10% | | | Fail |
| | 20% | | | Fail |
| | 30% | | | |
| | 40% | | | |
| | 50% | | | |

As shown by Table 6, microparticle formulations prepared from DL-PL, a 75:25 DL-PLG, and PCL were able to be administered through a 20 G needle using suspensions across a range of concentrations. However, these samples can only be administered through 21 G needles using dilute suspensions of 20% or less microparticle concentration in the injection vehicle.

These results are consistent with the practices used in the field with existing commercial products. Products that are typically prepared from DL-PLG copolymers are available commercially in kits that contain specific needles to be used to administer the product to the patient. These needles are typically in the size range of 19 G to 21 G.

Example 3

Microparticle Formulations Prepared from Admixtures of DL-PL and PCL that can Pass Through Smaller Diameter Needles Microparticle formulations were prepared based on compositions containing admixtures of DL-PL and PCL polymers containing ratios ranging from 95:5 to 50:50 of the DL-PL and PCL, respectively. Microparticle formulations were prepared as described above. These microparticle formulations were evaluated for syringe injectability using the 0.1 wt % TWEEN® 80 injection vehicle.

The microparticle formulations are described in Table 7 below, which also contains results from the injectability screening testing.

TABLE 7

| Batch information and injectability screening results of Example 3. | | | | | | |
|---|---|---|---|---|---|---|
| Formulation Parameters Needle size (Gauge) | Susp. conc., wt % | Admixture of: 95% DL-PL 5% PCL | Admixture of: 95% DL-PL 5% PCL | Admixture of: 90% DL-PL 10% PCL | Admixture of: 80% DL-PL 20% PCL | Admixture of: 50% DL-PL 50% PCL |
| Formulation lot number | | 0156-042 | 0156-090 | 0061-149 | 0061-151 | 0061-153 |
| Polymer component 1 | | 95% B | 95% V | 90% B | 80% B | 50% B |
| Polymer component 2 | | 5% C | 5% C | 10% C | 20% C | 50% C |
| Polymer component 3 | | | | | | |
| Dry sieve performed | | Yes (300 microns) | Yes (300 microns) | Yes (300 microns) | Yes (300 microns) | Yes (300 microns) |
| Mean particle size, microns | | 81.3 | 82.7 | 86.0 | 89.6 | 58.5 |
| D(90) particle size, microns | | 114.9 | 114.4 | 117.1 | 119.0 | 81.7 |
| 21 G | 10% | | | | | |
| | 20% | Pass | Pass | Pass | Pass | Pass |
| | 30% | | | Pass | Pass | Pass |
| | 40% | | | | | |
| | 50% | Pass | Pass | Pass | Pass | Pass |
| 23 G | 10% | | | Pass | Pass | Pass |
| | 20% | Pass | Pass | Pass | Pass | Fail |
| | 30% | | | | | |
| | 40% | | | | | |
| | 50% | Pass | Pass | Pass | Pass | Fail |
| 25 G | 10% | | | Fail | Fail | Fail |
| | 20% | Pass | Pass | | | |
| | 30% | Pass | Pass | | | |
| | 40% | Fail | Fail | | | |
| | 50% | | Fail | | | |
| 25 G-UTW | 10% | | | | | |
| | 20% | Pass | | | | |
| | 30% | Pass | | | | |
| | 40% | | | | | |
| | 50% | Pass | | | | |

As indicated in Table 7, two different microparticle compositions were prepared with a 95:5 ratio (by weight) of DL-PL and PCL, respectively. These two formulations differ in the DL-PL polymer sample that was used to prepare the two samples. The first sample listed in Table 7, formulation Lot 00156-042, was prepared from a high molecular weight DL-PL (having a reported inherent viscosity of 1.04 dL/g). In contrast, the second sample, formulation Lot 00156-090, was prepared using a (relatively) low molecular weight DL-PL (having a reported inherent viscosity of 0.35 dL/g). The viscosity typically ranges from about 0.15 dL/g to 2.0 dL/g.

Results of injectability screening of these microparticle compositions is in marked contrast to the results obtained from the standard microparticle compositions of the previous Example. In this case, it is found that microparticle compositions prepared from admixtures of DL-PL with at least small quantities of PCL provide dramatically improved injectability (defined as being able to pass through a smaller gauge needle) as compared to that of the samples from the previous Example. It has been demonstrated that microparticle compositions containing typically about 30% or less of the PCL constituent in these admixtures are able to be administered or injected through 23 G needles across all suspension concentration ranges that were investigated including suspensions containing 50% solids. This, in itself, is a dramatic improvement over the results from the previous Example.

Further, it has been shown that admixtures in the range of about 95:5 weight ratio of DL-PL and PCL, respectively, provide even further improvements in performance in the injectability screening testing. The enhanced injectability effect was demonstrated by testing of two different batches of the 95:5 microparticle compositions as shown in Table 7. Microparticle formulations prepared from these compositions of DL-PL and PCL were able to be administered or injected through 25 G needles at suspension concentration ranges as high as 30% and, in one case, through 25 G-TW needles at all concentration levels tested (see Table 7) These results demonstrate the reproducibility of the effect, particularly across a range of molecular weights of the DL-PL component used to prepare these two formulations.

Example 4

Capillary Viscometry of DL-PL/PCL Microparticle Formulations

To further characterize these compositions, capillary viscometry was conducted on concentrated suspensions of microparticle formulations in the same injection vehicle as that used to generate the injectability screening results, 0.1 wt % TWEEN® 80 vehicle.

Results of capillary viscometry on the injection vehicle itself and on 40% suspensions of microparticle formulations in the injection vehicle are presented in Table 8.

TABLE 8

| Capillary viscometry fall times of suspensions of prepared from microparticle compositions containing admixtures of DL-PL and PCL of Example 4. | | |
|---|---|---|
| Sample description | Microparticle formulation lot number | Fall time, seconds (mean ± sd) |
| Injection vehicle only | — | 34 ± 1 |
| 75:25 DL-PLG microparticle formulation | 0061-020 | 400 ± 3 |
| 95:5 admixture of DL-PL and PCL | 0156-042 | 300 ± 8 |
| 90:10 admixture of DL-PL and PCL | 0061-149 | 385 ± 5 |

The fall time of a suspension prepared from a 75:25 DL-PLG copolymer (from the earlier Example) was 400 seconds. In contrast, the fall time of a microparticle composition prepared from the 95:5 admixture of the DL-PL and PCL polymers was found to be 300 seconds. These numbers indicate a significant difference in flow characteristics between these two microparticle suspensions. The microparticle composition having the fastest capillary viscometer flow is also the composition that has the most significant improvement in flow through the syringe needles. It is also useful to point out that the microparticle composition having intermediate injectability results, namely, the 90:10 admixture of the DL-PL and the PCL polymer (microparticle lot number 0061-149) exhibited a capillary viscometry fall time that was also intermediate (385 seconds).

The viscometry method that was used employed a #150 sized capillary tube. The #150 designation refers to the inside diameter of the capillary used in the fabrication of the capillary viscometer; in the case of a size #150 tube, the inside diameter is reported to be 0.78 mm (780 microns) according to ASTM Test Method D446. This size falls in the range of the inside diameters of 19 G to 20 G-TW needles which was in the range of about 580-800 microns. Consequently, it is reasonable that the flow characteristics of a suspension through a #150 capillary tube should reflect in some manner the flow of the same suspension through a syringe needle.

Example 5

Injectability of Small Particle Size Fractions of Microparticle Formulations Two microparticle formulations were made as described above except that the collection step was carried out using test sieves or screens having mesh size of 45 and 20 microns. In this manner, microparticle product was obtained that specifically contained a smaller particle size distribution than the standard formulations tested previously. One formulation was prepared from a 75:25 DL-PLG and the second was prepared containing a 95:5 blend of DL-PL and PCL. This was carried out to investigate whether there was any appreciable difference in injectability between these two representative microparticle compositions when changing particle size range and when testing with very small-diameter needles.

These microparticle formulations were evaluated for syringe injectability using the 0.1 wt % TWEEN® 80 injection vehicle. Injectability screening was conducted on these microparticle formulations. Injectability testing was carried out in this example using small-diameter that were 25 G, 26 G-TW (thin wall), and 27 G needles.

Results of injectability testing for the two microparticle compositions are summarized in Table 9.

TABLE 9

| Injectability results of small particle size (20-45 micron) microparticle formulations of Example 5 | | | |
|---|---|---|---|
| Formulation Parameters Needle size (Gauge) | Suspension conc., wt % | 75:25 DL-PLG | Admixture of: 95% DL-PL 5% PCL |
| Formulation lot number | | 0156-120 | 0156-122 |
| Polymer component 1 | | 100% A | 95% B |
| Polymer component 2 | | | 5% C |
| Mean particle size, microns | | 33..6 | 32.1 |
| D(90) particle size, microns | | 39.2 | 39.3 |
| Dry sieve performed | | None | None |
| 26 G-Thin Wall (TW) | 10% | Pass | Pass |
| | 20% | Fail | Pass |
| | 30% | Fail | Pass |
| | 40% | | |
| | 50% | Fail | Pass |
| 27 G | 5% | Pass | Pass |
| | 10% | Fail [1] | Fail [1] |
| | 20% | Fail | Fail |

NOTE:
[1] In 5 replicate trials using a suspension concentration of 10%, the 75:25 DL-PLG formulation had 0/5 replicate samples that passed the injectability criteria while the formulation comprised of the 95:5 polymer blend had 2/5 replicate samples that passed the injectability criteria.

It has been shown that smaller particle size fractions of microparticle compositions prepared from the admixture of DL-PL and PCL exhibit improved injectability over other microparticle compositions such as the 75:25 DL-PLG. Results in Table 9 shows that the 20- to 45-micron size fraction of the DL-PL/PCL composition exhibits good injectability through 26-G-TW needles at all suspension concentrations tested. In comparison, the 75:25 DL-PLG formulation can only be injected through the 26 G-TW needle at the lowest-solids suspension tested.

Additional injectability testing on these two formulations showed that 2 out of 5 replicate trials conducted on the DL-PL/PCL composition passed the injectability screening test while 0 out of 5 trials passed when testing was performed with the 75:25 DL-PLG composition (Table 9).

Example 6

Drug-Loaded Microparticle Formulations Prepared from Admixtures of DL-PL and PCL (Nalmefene Base and Goserelin Acetate)

Several drug-containing microparticle formulations were prepared to show improved injectability effect with microparticles. A small-molecule drug, nalmefene base, was used in addition to a bioactive peptide, goserelin acetate, to prepare representative drug-containing microparticle formulations.

Microparticle formulations were prepared by the method of Example 2 using methylene chloride and DP polymer solution concentrations of 20%. Input loading levels of nalmefene base and goserelin acetate were 10% and 5%, respectively. The measured loading levels of nalmefene and goserelin in the dried microsphere product was 5.6 wt % and 2.5 wt %, respectively.

These microparticle formulations were evaluated for syringe injectability using the 0.1 wt % TWEEN® 80 injection vehicle. The results of injectability screening testing are shown in Table 10.

TABLE 10

Batch information and injectability results of Example 6.

| Formulation Parameters Needle size (Gauge) | Suspension conc., wt % | 75:25 DL-PLG | Nalmefene in admixture of: 95% DL-PL 5% PCL | Goserelin in admixture of: 95% DL-PL 5% PCL |
|---|---|---|---|---|
| Formulation lot number | | 0156-046 | 0156-110 | 0156-112 |
| Polymer component 1 | | 100% A | 95% B | 95% B |
| Polymer component 2 | | | 5% C | 5% C |
| Polymer component 3 | | | | |
| Dry sieve performed | | Yes (212 micron) | Yes (300 micron) | Yes (300 micron) |
| Mean particle size, microns | | 78.2 | 78.9 | 62.8 |
| D(90) particle size, microns | | 114.6 | 113.1 | 108.0 |
| Drug loading | | Nalmefene base (5.3 wt %) | Nalmefene base (5.6 wt %) | Goserelin (2.5 wt %) |
| 21 G | 10% | | | |
| | 20% | Pass | Pass | Pass |
| | 30% | | | |
| | 40% | | | |
| | 50% | Fail | Pass | Pass |
| 23-G | 10% | Fail | | |
| | 20% | Fail | Pass | Pass |
| | 30% | | | |
| | 40% | | | |
| | 50% | Fail | Pass | Pass |
| 25 G | 10% | Fail | | |
| | 20% | | Pass | Pass |
| | 30% | | Fail | Fail |
| | 40% | | | |
| | 50% | | Fail | Fail |
| 25 G-UTW | 10% | | Pass | Pass |
| | 20% | | Pass | |
| | 30% | | Pass | |
| | 40% | | | |
| | 50% | | Pass | Pass |
| 26 G TW | 10% | | Pass | Pass |
| | 20% | | Pass | Pass |
| | 30% | | Fail | Fail |
| | 40% | | | |
| | 50% | | | |

Enhanced injectability is shown for a microparticle composition comprising the admixture of the DL-PL and PCL polymers. Further demonstration of the enhanced injectability has been shown in Table 10 using needles with sizes of 25 G, 25 G-UTW (ultra thin wall needles), and 26 G-TW (thin wall).

Capillary viscometry of a microparticle suspension of a formulation prepared using 10% nalmefene base (Lot 0156-110) was determined to be 305 seconds (Table 11). This result supports the trend whereby formulations that exhibit improved injectability also exhibit a fast capillary viscometry fall time.

TABLE 11

Capillary viscometry data for 10% nalmefene base in 95:5 admixture of DL-PL and PCL

| Microparticle formulation composition | Microparticle lot number | Fall time, seconds (mean ± sd) |
|---|---|---|
| 10% nalmefene base with 95:5 admixture of DL-PL and PCL | 0156-110 | 305 ± 1 |

Example 7

Effects of Terminal Sterilization Treatment

A portion of a microparticle composition that was prepared using the 95:5 admixture of the DL-PL and PCL polymers (Lot 0156-042) was exposed to 2.5 Mrad gamma-irradiation as a means of terminal sterilization. Irradiation was performed by Neutron Products (Dickerson, Md.) on samples that were frozen on dry ice prior to and during the irradiation operation. Dosimeters included in the actual irradiation container indicated that samples were exposed to an actual dose in the range of about 2.53-2.66 Mrad.

These microparticle formulations were evaluated for syringe injectability using the 0.1 wt % TWEEN® 80 injection vehicle. Injectability screening was conducted on these microparticle formulations. Samples were tested for injectability as they were received following the gamma-irradiation process; no additional sieving operation was carried out on the samples after treatment to the sterilization operation.

The results of injectability screening testing are shown in Table 12 and demonstrate that the improved injectability of the microparticle composition is retained after exposure to the gamma-irradiation process.

TABLE 12

| Effects of terminal sterilization on injectability effects of Example 7. | | | |
|---|---|---|---|
| Formulation Parameters Needle size (Gauge) | Suspension conc., wt % | Admixture of: 95% DL-PL 5% PCL | Admixture of: 95% DL-PL 5% PCL |
| Lot Number | | 0156-042 | 0156-042 |
| Polymer component 1 | | 95% B | 95% B |
| Polymer component 2 | | 5% C | 5% C |
| Polymer component 3 | | | |
| Sieve conditions | | Yes (300 micron) | Yes (300 micron) |
| Particle size 90% | | | |
| Mean particle size, microns | | 81.3 | 82.5 |
| D(90) particle size, microns | | 114.9 | 118.1 |
| Drug loading | | None | None |
| Terminal Sterilization treatment? | | No | Yes |
| 21 G | 10% | | |
| | 20% | Pass | |
| | 30% | | |
| | 40% | | |
| | 50% | Pass | Pass |
| 23 G | 10% | | |
| | 20% | Pass | |
| | 30% | | |
| | 40% | | |
| | 50% | Pass | Pass |
| 25 G | 10% | | |
| | 20% | Pass | Pass |
| | 30% | Pass | Pass |
| | 40% | Fail | Fail |
| | 50% | | |

Example 8

Admixtures of DL-PL and PCL with Other Polymers

The method can be further expanded by combining admixtures of DL-PL and PCL with other suitable medical or pharmaceutical polymers or biocompatible polymers in the preparation of the microparticle composition. Microparticle compositions were prepared as follows. An admixture consisting of 75% DL-PL and 25% PCL (by weight) was combined with a 75:25 poly(DL-lactide-co-glycolide) (PLG) copolymer. This polymer blend was then used to prepare microparticle compositions using methylene chloride and DP polymer solution concentrations of 20%. The microparticle composition was prepared using a ratio of 90% by weight of the PLG copolymer with the remaining 10% of the polymer composition consisting of the admixture of the DL-PL and the PCL polymers. Based on these ratios, the microparticle composition was prepared using a ratio (by weight) of approximately 90% PLG, 7.5% DL-PL, and 2.5% PCL.

These microparticle formulations were evaluated for syringe injectability using the 0.1 wt % TWEEN® 80 injection vehicle. Injectability screening was conducted. The microparticle compositions prepared and analyzed in this Example are shown in Table 13.

TABLE 13

| Batch information and injectability results of Example 8. | | | | |
|---|---|---|---|---|
| Formulation Parameters Needle size (Gauge) | Susp. conc., wt % | Admixture of: 90% 75:25 PLG 7.5% DL-PL 2.5% PCL | Admixture of: 90% 75:25 PLG 7.5% DL-PL 2.5% PCL | Admixture of: 90% 75:25 PLG 7.5% DL-PL 2.5% PCL |
| Formulation lot number | | 0061-123 | 0156-108 | 0061-127 |
| Polymer component 1 | | 90% A | 90% A | 90% A |
| Polymer component 2 | | 7.5% B | 7.5% B | 7.5% V |
| Polymer component 3 | | 2.5% C | 2.5% C | 2.5% C |
| Dry sieve performed | | Yes (300 microns) | Yes (300 microns) | Yes (300 microns) |
| Mean particle size, microns | | 70.3 | 74.9 | 79.5 |
| D(90) particle size, microns | | 107.5 | 106.6 | 110.6 |
| 21 G | 10% | | | |
| | 20% | | | |
| | 30% | | | |
| | 40% | | | |
| | 50% | Pass | Pass | Pass |
| 23 G | 10% | | | |
| | 20% | Pass | Pass | Pass |
| | 30% | | | |
| | 40% | Pass | Pass | Pass |
| | 50% | Pass | Pass | Pass |
| 25 G | 10% | Pass | Pass | Pass |
| | 20% | Fail | Fail | Fail |
| | 30% | | Fail | |
| | 40% | | Fail | |
| | 50% | | | |
| 25 G-UTW | 10% | | Pass | |
| | 20% | | Pass | |
| | 30% | | Pass | |
| | 40% | | Fail | |
| | 50% | | Fail | |

The first two microparticle formulations are replicate preparations of the same admixture of polymers. The third formulation in Table 13 was prepared with a low molecular weight DL-PL in order to evaluate the reproducibility of the effect with changes to the molecular weight of the constituent polymers. The results in Table 13 demonstrate that these microparticle compositions can be administered through 23-G needles across all suspension concentration ranges investigated and, further, that that dilute suspensions (for example, suspensions containing 10% solids) can be injected through 25-G needles as well. Additionally, trials conducted with a 25 G-UTW needle were successful in delivering suspensions at concentrations up to 30% solids. These results, both in terms of the needle size (Gauge) and the suspension concentration levels, demonstrate significantly improved or enhanced injectability in comparison to that of more traditional microparticle compositions described above.

Capillary viscometry of a microparticle suspension of microparticle formulation 0156-108 was determined to be 310 seconds (Table 14). This result supports the trend identified in Example 9 whereby formulations that exhibit improved injectability also exhibit a correspondingly fast capillary viscometry fall time.

TABLE 14

| Capillary viscometry data for 90:10 admixture of DL-PL and DL-PL/PCL blend | | |
|---|---|---|
| Microparticle formulation composition | Microparticle lot number | Fall time, seconds (mean ± sd) |
| 90% 75:25 PLG and 10% DL-PL/PCL blend | 0156-108 | 310 ± 2 |

Example 9

Microparticle Compositions Prepared with Copolymers of Lactide, Glycolide, and Caprolactone Microparticle compositions were prepared with copolymers of DL-lactide and caprolactone or copolymers of DL-lactide (DL-L), glycolide (G), and caprolactone (CPL). Three copolymers of DL-L, G, and CPL and one copolymer of DL-L and CPL were made. In general, these copolymers are all rich in lactide (relative to the total content of lactide and caprolactone).

Microparticle compositions were made with only copolymers. Several microparticle compositions also were made from admixtures of copolymer with another standard medical or pharmaceutical polymer, a 75:25 DL-PLG polymer at a 90:10 ratio, by weight, of the DL-PLG to the copolymer, respectively. Microparticle compositions were prepared using methylene chloride and DP polymer solution concentrations of 20%.

These microparticle formulations were evaluated for syringe injectability using the 0.1 wt % TWEEN® 80 injection vehicle. Injectability screening was conducted on these microparticle formulations. The microparticle compositions prepared and analyzed in this Example are shown in Table 15.

TABLE 15

Batch information and injectability results from Example 9.

| Formulation Parameters Needle size (Gauge) | Susp. conc., wt % | 100% Copolymer of 70:24:06 DL-L:G:CPL | Admixture of: 90% 75:25 PLG 10% 75:25 DL-PL:CPL Copolymer | Admixture of: 90% 75:25 PLG 10% 38:38:24 Copolymer | Admixture of: 90% 75:25 PLG 10% 38:38:24 Copolymer |
|---|---|---|---|---|---|
| Formulation lot number | | 0156-022 | 0061-063 | 0156-030 | 0156-028 |
| Polymer component 1 | | 100% S | 90% A | 90% A | 90% A |
| Polymer component 2 | | | 10% I | 10% T | 10% U |
| Polymer component 3 | | | | | |
| Dry sieve performed | | Yes (212 microns) | None | Yes (212 microns) | Yes (212 microns) |
| Mean particle size, microns | | 74.0 | 89.0 | 62.2 | 65.0 |
| D(90) particle size, microns | | 104.9 | 120.6 | 99.9 | 97.6 |
| 21G | 10% | | | | |
| | 20% | Pass | | Pass | Pass |
| | 30% | | | | |
| | 40% | | | | |
| | 50% | Pass | Pass | Pass | Pass |
| 23G | 10% | | | | |
| | 20% | Pass | Pass | Pass | Pass |
| | 30% | | | | |
| | 40% | | | | |
| | 50% | Pass | Pass | Pass | Pass |
| 25G | 10% | | | | |
| | 20% | Pass | Pass | Pass | Pass |
| | 30% | Pass | | Pass | Fail |
| | 40% | Fail | | Fail | Fail |
| | 50% | Fail | Fail | Fail | Fail |

Microparticle compositions prepared with copolymers having high ratios of lactide:caprolactone exhibit improved injectability properties. Injectability of these formulations was demonstrated through 23 G needles at all concentration ranges tested. Injectability was demonstrated through 25 G needles at the 20% or 30% solids.

The copolymer compositions are identified in Table 16. The percent of lactide relative to the combined amount of lactide and caprolactone was calculated to demonstrate that the lactide and caprolactone composition of these copolymers reflects that of the advantageous compositions tested in earlier examples.

TABLE 16

Copolymer compositions

| DL-L:G:CPL, mole ratio in the copolymer | Polymer sample reference (from Example 1) | Lactide content (relative to combined lactide and caprolactone constituents) |
|---|---|---|
| 75:0:25 | I | 75% lactide |
| 70:24:06 | S | 92% lactide |
| 38:38:24 | T | 61% lactide |
| 67:08:25 | U | 73% lactide |

The admixtures of Example 7 contained 7.5% DL-PL and 2.5% PCL which has a combined lactide content of about 75%; admixtures from this example that provided the improved injectability effect contained 80% to about 95% of the lactide component, the DL-PL polymer. Consequently, microparticle compositions which contain, either in their entirety or when blended with other medical or pharmaceutical polymers, ratios of DL-PL and caprolactone that are rich in lactide have been found to exhibit the improved injectability effect. This effect is also found from similar microparticle compositions that are prepared using copolymers that are rich in lactide relative to caprolactone, for example, lactide content of about 60% and above relative to the combined lactide and caprolactone content.

Example 10

Blends of Different Microparticle Compositions

A portion of a microparticle formulation which, on its own, exhibits the improved injectability effect, i.e., particle composition can be injected through a smaller gauge needle than expected, was blended with a microparticle formulation prepared from standard biodegradable polymer that, on its own, exhibits poor injectability properties. In this manner, blending of multiple microparticle formulations was examined to identify whether blending can be used as a strategy to improve the overall injectability.

A 75:25 DL-PLG formulation which exhibits poor injectability (Lot 0156-006) was used. Two separate blends of microparticle formulations were then prepared using a small proportion (25%, by weight) of either of two microparticle formulations that demonstrate, on their own, improved injectability. These two formulations included a microparticle composition consisting of a 95:5 blend of DL-PL:PCL (Lot 0156-090) and a composition consisting of the 70:24:06 copolymer (Lot 0156-022). Blends of the microsphere formulations were prepared containing 75% of the DL-PLG formulation. Blending was conducted by weighing out the indicated amount of each microparticle formulation into the syringe during preparation of the test syringes 5. The dry microparticle formulations were then evaluated for syringe injectability using the 0.1 wt % TWEEN® 80 injection vehicle.

The samples tested are described in Table 17. Table 17 also shows the results of the injectability screening testing.

TABLE 17

Batch information and injectability results from Example 10.

| Formulation Parameters Needle size (Gauge) | Susp. Conc. | 75:25 DL-PLG | Blends of microparticle formulations: 75%: 75:25 DL-PLG 25%: 95:5 DL-PL/PCL | Blends of microparticle formulations: 75%: 75:25 DL-PLG 25%: 70:24:06 Copolymer |
|---|---|---|---|---|
| | | — | | — |
| Microparticle formulation component 1 | | 100% 00156-006 (DL-PLG) | 75% 0156-006 | 75% 0156-006 |
| Microparticle formulation component 2 | | | 25% 0156-090 | 25% 0156-022 |
| Dry sieve performed | | Yes (300 micron) | Yes (300 micron) | Yes (300 micron) |
| Mean particle size, microns | | na | na | na |
| D(90) particle size, microns | | na | na | na |
| Drug loading | | None | None | None |
| 21 G | 10% | | | |
| | 20% | Pass | Pass | Pass |
| | 30% | | | |
| | 40% | | | |
| | 50% | Pass | | |
| 23 G | 10% | Fail | | |
| | 20% | Fail | Pass | Pass |
| | 30% | | Pass | Pass |
| | 40% | | Pass | Pass |
| | 50% | Fail | Fail | Fail |
| 25 G | 10% | | Fail | Fail |
| | 20% | | | |
| | 30% | | | |
| | 40% | | | |
| | 50% | | | |

NOTES:
"na" indicates that particle sizes were not determined on blends of individual microparticle formulations; refer to particle size results from individual batches used to prepare these blends.

Results demonstrate that the 75:25 DL-PLG formulation can only be injected through 21 G needles at the concentration levels tested. Blending this formulation with only 25% of a second microparticle formulation was successful in achieving injectability through a 23 G needle up to 40% solids.

Example 11

Alternate Processing Solvent

A microparticle composition was prepared using ethyl acetate as the Dispersed Phase (DP) processing solvent. This microparticle formulation was evaluated for syringe injectability using the 0.1 wt % TWEEN® 80 injection vehicle. Injectability screening was conducted.

For comparison purposes, the same microparticle composition prepared from methylene chloride (Lot 0156-022) was tested.

The results of injectability testing of the microparticle composition prepared from ethyl acetate are shown in Table 18 and demonstrate that the enhanced injectability effect is retained when the microparticle composition is prepared using an alternate solvent system.

TABLE 18

| Batch information and injectability results from Example 11. | | |
|---|---|---|
| Formulation Parameters Needle size (Gauge) | Susp. conc., wt % | 100% Copolymer of 70:24:06 DL-L:G:CPL |
| Formulation lot number | | 0156-106 |
| Polymer component 1 | | 100% S |
| Polymer component 2 | | |
| Polymer component 3 | | |
| DP processing solvent | | Ethyl Acetate |
| Dry sieve performed | | Yes (300 microns) |
| Mean particle size, microns | | 68.8 |
| D(90) particle size, microns | | 108.0 |
| 21 G | 10% | |
| | 20% | Pass |
| | 30% | |
| | 40% | |
| | 50% | Pass |
| 23 G | 10% | |
| | 20% | Pass |
| | 30% | |
| | 40% | |
| | 50% | Pass |
| 25 G | 10% | |
| | 20% | Pass |
| | 30% | Fail |
| | 40% | |
| | 50% | Fail |
| 25 G-UTW | 10% | Pass |
| | 20% | |
| | 30% | |
| | 40% | |
| | 50% | Pass |

Example 12

Injection Vehicle Composition

Injectability testing was carried out on formulation Lot 0156-108 using an alternative injection vehicle composition containing sodium dodecylsulfate (SDS) in place of TWEEN® 80.

Capillary viscometry of this microparticle formulation (Lot 0156-108) using a 40% suspensions in the SDS injection vehicle exhibited a capillary fall time similar to that of the same formulation tested using the TWEEN® 80 injection vehicle (Example 8) is shown in Table 19.

TABLE 19

Capillary viscometry measurement of particles prepared from 95% DL-PL and 5% PCL

| Microparticle formulation composition | Microparticle lot number | Injection vehicle surfactant | Fall time, seconds (mean ± sd) |
|---|---|---|---|
| 95% DL-PL and 5% PCL | 0156-108 | SDS | 320 ± 2 |

Example 13

Injectability Testing of Representative Microparticle Formulations Prepared from Poly(4-Hydroxybutyrate) Biodegradable Polymers TEPHAFLEX® and TEPHELAST® P4HB polymers were obtained having relatively low and high molecular weights (approximately 150 kDa for low molecular weight and approximately 400 kDa for high molecular weight). In addition, TEPHELAST® copolymer samples were obtained having 20% and 30% 4-hydroxybutyrate content with the remainder being 3-hydroxybutyrate. Microparticle formulations were prepared from these different materials. The dry microparticle formulations were then evaluated for syringe injectability using the 0.1 wt % TWEEN® 80 injection vehicle.

Microparticle formulations prepared from the TEPHAFLEX® and TEPHELAST® poly(4-hydroxybutyrate) biodegradable polymers and results of injectability screening are described in Table 20.

TABLE 20

Batch information and injectability screening results for Example 13.

| Formulation Parameters Needle size (Gauge) | Susp. Conc. | TephaFLEX ® (low MW) | TephaFLEX ® (high MW) | TephELAST 20% (low MW) | TephELAST 20% (high MW) | TephELAST 30% (low MW) | TephELAST 30% (high MW) |
|---|---|---|---|---|---|---|---|
| Formulation lot number | | 0037-023 | 0037-021 | 00156-032 | 00156-092-00 | 00156-034 | 0037-029 |
| Polymer component 1 | | 100% D | 100% E | 100% P | 100% Z | 100% O | 100% F |
| Polymer component 2 | | | | | | | |
| Polymer component 3 | | | | | | | |
| Dry sieve performed | | None | None | Yes (212 micron) | Yes (300 micron) | Yes (212 micron) | None |
| Mean particle size, microns | | 64.0 | 82.0 | 55.0 | 90.3 | 87.3 | 53.0 |
| D(90) particle size, microns | | 99.0 | 133.0 | 88.6 | 119.3 | 122.0 | 92.6 |
| 21 G | 10% | | | | | | |
| | 20% | Pass | Fail | Pass | Pass | Pass | Pass |
| | 30% | Fail | | | | | Pass |
| | 40% | | | | | | |
| | 50% | | | Pass | Pass | Pass | Pass |

TABLE 20-continued

Batch information and injectability screening results for Example 13.

| Formulation Parameters Needle size (Gauge) | Susp. Conc. | TephaFLEX ® (low MW) | TephaFLEX ® (high MW) | TephELAST 20% (low MW) | TephELAST 20% (high MW) | TephELAST 30% (low MW) | TephELAST 30% (high MW) |
|---|---|---|---|---|---|---|---|
| 23 G | 10% | | | | Pass | | |
| | 20% | Fail | | Pass | Fail | Pass | |
| | 30% | | | Fail | | Pass | |
| | 40% | | | Fail | | Fail | |
| | 50% | | | Fail | Fail | Fail | Pass |
| 25 G | 10% | | | Fail | | Fail | |
| | 20% | | | | Fail | | Pass |
| | 30% | | | | | | |
| | 40% | | | | | | |
| | 50% | | | | | | Pass |

Microparticle formulations consisting of the TEPHAFLEX® polymers did not exhibit any improved injectability performance relative to samples prepared from the prior art polymers from Example 2.

In contrast, microparticle compositions prepared with the TEPHELAST® copolymers generally exhibited enhanced injectability. In all cases, microparticles prepared from the TEPHELAST® copolymers were able to be injected through 21 G needles at all solids levels tested and through 23 G needles from all microparticle suspensions.

More notably, the microparticle formulation prepared using the high molecular weight TephELAST 30% copolymer exhibited significantly improved injectability over the other samples investigated. In this case, injectability was achieved through both 23 G and 25 G needles at all solids levels tested.

Example 14

Injectability Testing of Microparticle Formulations Prepared from Blends of the TephELAST 30% Copolymer with a 75:25 DL-PLG at Different Blend Ratios The high-molecular-weight TEPHELAST® 30% copolymer was blended with a 75:25 copolymer of poly(DL-lactide-co-glycolide) (DL-PLG) at different blend ratios ranging from about 5%, to 25% (by weight) of the TEPHELAST® polymer. The microparticles were then evaluated for syringe injectability using the 0.1 wt % TWEEN® 80 injection vehicle. Replicate microparticle formulations were prepared at the composition ratios of 10% and 25% to demonstrate the reproducibility of the effects. The results are shown in Table 21.

TABLE 21

Batch information and injectability screening results of Example 14.

| Formulation Parameters Needle size (Gauge) | Susp. Conc. | 75%: 75:25 DL-PLG 25%: TephELAST | 75%: 75:25 DL-PLG 25% TephELAST | 90%: 75:25 DL-PLG 10% TephELAST | 90%: 75:25 DL-PLG 10% TephELAST | 95%: 75:25 DL-PLG 5%: TephELAST |
|---|---|---|---|---|---|---|
| Formulation lot Number | | 0061-113 | 0061-143 (replicate of 0061-113) | 0037-147 | 0061-137 (replicate of 0037-147) | 0061-115 |
| Polymer component 1 | | 75% A | 75% A | 90% A | 90% A | 95% A |
| Polymer component 2 | | 25% F | 25% F | 10% F | 10% F | 5% F |
| Polymer component 3 | | | | | | |
| Dry sieve performed | | None | None | None | Yes (300 micron) | None |
| Mean particle size, microns | | 84.6 | 94.8 | 91.5 | 95.8 | 76.2 |
| D(90) particle size, microns | | 118.6 | 124.4 | 122.2 | 124.8 | 118.9 |
| 21 G | 10% | | | | | |
| | 20% | | | Pass | Pass | |
| | 30% | | | | | |
| | 40% | | | | | |
| | 50% | Pass | Pass | Pass | Pass | Pass |
| 23 G | 10% | | | | | |
| | 20% | Pass | Pass | | | Fail |
| | 30% | | | | | |
| | 40% | Fail | Pass | | | Fail |
| | 50% | Pass | | Pass | Pass | |

TABLE 21-continued

Batch information and injectability screening results of Example 14.

| Formulation Parameters Needle size (Gauge) | Susp. Conc. | 75%: 75:25 DL-PLG 25%: TephELAST | 75%: 75:25 DL-PLG 25% TephELAST | 90%: 75:25 DL-PLG 10% TephELAST | 90%: 75:25 DL-PLG 10% TephELAST | 95%: 75:25 DL-PLG 5%: TephELAST |
|---|---|---|---|---|---|---|
| 25 G | 10% | Pass | Pass | | | |
| | 20% | Pass | Pass | Pass | Pass | Fail |
| | 30% | | | | Fail | Fail |
| | 40% | | | Fail | | |
| | 50% | Fail | Fail | | Fail | |

As shown by Table 21, blending the TEPHELAST® 30% copolymer into a representative DL-PLG improved the injectability of microparticle formulations. Samples containing 10-25% of the TEPHELAST® copolymer showed improved injectability over formulations prepared from standard polyesters.

The "fail" result reported in the 23-G needle at the 40% suspension concentration level for Lot 0061-113 containing 25% of the TEPHELAST® appears to be an artifact result attributable to a small amount of aggregation in the laboratory sample prior to injectability testing; additional testing at higher concentration levels and with smaller-diameter needles provided "pass" results under these more challenging test conditions. Further, testing of the replicate batch (Lot 0061-143) demonstrated "pass" results under all these test conditions. Otherwise, replicate batches prepared with 10% and 25% of the TEPHELAST® copolymer demonstrated the reproducibility of the effect between microparticle formulations. Further, the dry-sieving procedure conducted on the replicate lot of the 10% blend did not demonstrate any notable change in the injectability effect demonstrating the sieving operation did not appear to skew or alter the extent of the effect to any noticeable degree.

Example 15

Injectability Testing of Microparticle Formulations Prepared from Blends Containing 10% (by Weight) of the TEPHELAST® 30% Copolymer in Standard Biodegradable Polymer of Varying Lactide:Glycolide Copolymer Composition A series of microparticle formulations was prepared from polymer blends containing 10% high molecular weight TEPHELAST® 30% copolymer with a DL-PL polymer or a 65:36 DL-PLG or a 50:50 DL-PLG. Additionally, a microparticle formulation has also been prepared from a similar blend using an acid end-group 75:25 DL-PLG copolymer.

The dry microparticle formulations were evaluated for syringe injectability using the 0.1 wt % TWEEN® 80 injection vehicle.

Microparticle formulations prepared with 10% of the TEPHELAST® polymer blended with the various DL-PL and DL-PLG polymers and the results of injectability screening are described in Table 22. Included in Table 22 for comparison purposes is the information and the test results on Lot 0061-137.

TABLE 22

Batch information and injectability screening results from Example 15.

| Formulation Parameters Needle size (Gauge) | Susp Conc. | 90%: DL-PL 10% TephELAST | 90%: 75:25 PLG 10%: TephELAST | 90%: 75:25 PLG (acid end-group polymer) 10%: TephELAST | 90%: 65:35 PLG 10%: TephELAST | 90%: 50:50 PLG 10%: TephELAST |
|---|---|---|---|---|---|---|
| Formulation lot Number | | 0061-129 | 0061-137 | 0061-135 | 0061-131 | 0061-133 |
| Polymer component 1 | | 75% B | 90% A | 90% Y | 90% X | 90% W |
| Polymer component 2 | | 25% F | 10% F | 10% F | 10% F | 10% F |
| Polymer component 3 | | | | | | |
| Dry sieve performed | | Yes (300 micron) | Yes (300 micron) | Yes (300 micron) | Yes (300 micron) | Yes (300 micron) |
| Mean particle size, microns | | 70.0 | 95.8 | 83.1 | 77.8 | 73.2 |
| D(90) particle size, microns | | 121.7 | 124.8 | 115.0 | 110.3 | 112.8 |
| 21 G | 10% | | | | | |
| | 20% | | Pass | | | |
| | 30% | | | | | |
| | 40% | | | | | |
| | 50% | Pass | Pass | Pass | Pass | Pass |

TABLE 22-continued

Batch information and injectability screening results from Example 15.

| Formulation Parameters Needle size (Gauge) | Susp Conc. | 90%: DL-PL 10% TephELAST | 90%: 75:25 PLG 10%: TephELAST | 90%: 75:25 PLG (acid end-group polymer) 10%: TephELAST | 90%: 65:35 PLG 10%: TephELAST | 90%: 50:50 PLG 10%: TephELAST |
|---|---|---|---|---|---|---|
| 23 G | 10% | | | | | |
| | 20% | Pass | | Pass | Pass | Fail |
| | 30% | | | | | |
| | 40% | Pass | | Pass | Pass | Fail |
| | 50% | | Pass | | | |
| 25 G | 10% | Pass | | Pass | Pass | Fail |
| | 20% | Pass | Pass | Pass | Fail | Fail |
| | 30% | | Fail | | | |
| | 40% | | | | | |
| | 50% | | Fail | Fail | Fail | Fail |

Improved injectability was observed in blends with all of the DL-PL and DL-PLG polymer compositions. The microparticle compositions prepared from blends with all of the DL-PL and DL-PLG materials were deliverable through a 21 G needle at a very high concentration level (50 wt %). Further, improved injectability was observed through 23 G needles at all concentrations tested and through 25 G needles for dilute suspensions for all microparticle compositions that were prepared from blends comprised of a DL-PLG copolymer having a lactide:glycolide ratio from 65:35 through to 100:0 (the DL-PL).

Example 16

Injectability Testing of Microparticle Formulations Prepared with a Model Drug, Nalmefene Base Two microparticle formulations were prepared using the TEPHELAST® polymer and with nalmefene base as a model drug to evaluate whether the enhanced injectability was also obtained with drug-loaded microparticle formulations. The dry microparticle formulations were then evaluated for syringe injectability using the 0.1 wt % TWEEN® 80 injection vehicle.

Microparticle formulations prepared with nalmefene base are described in Table 23. For reference, included in Table 23 are the results of testing of a DL-PLG sample (Lot 0156-046).

TABLE 23

Batch information and injectability screening results from Example 16.

| Formulation Parameters Needle size (Gauge) | Susp Conc. | 75:25 DL-PLG | TephELAST | 75:25 DL-PLG TephELAST |
|---|---|---|---|---|
| Formulation lot Number | | 0156-046 | 0156-058 | 0156-48 |
| Polymer component 1 | | 100% A | 100% F | 90% A |
| Polymer component 2 | | | | 10% F |
| Polymer component 3 | | | | |
| Dry sieve performed | | Yes (212 micron) | Yes (212 micron) | Yes (212 micron) |
| Mean particle size, microns | | 78.7 | 78.2 | 62.5 |
| D(90) particle size, microns | | 114.6 | 110.8 | 101.0 |
| Drug loading, wt % (nalmefene) | | 5.3 | 6.2 | 3.8 |

TABLE 23-continued

Batch information and injectability screening results from Example 16.

| Formulation Parameters Needle size (Gauge) | Susp Conc. | 75:25 DL-PLG | TephELAST | 75:25 DL-PLG TephELAST |
|---|---|---|---|---|
| 21 G | 10% | | | |
| | 20% | Pass | Pass | Pass |
| | 30% | | | |
| | 40% | | | |
| | 50% | Fail | Pass | Pass |
| 23 G | 10% | Fail | | |
| | 20% | Fail | Pass | Pass |
| | 30% | | | |
| | 40% | | | |
| | 50% | Fail | Pass | Pass |
| 25 G | 10% | Fail | Fail | Fail |
| | 20% | | Fail | Fail |
| | 30% | | | |
| | 40% | | | |
| | 50% | | Fail | Fail |

Included in Table 23 are results of testing of a DL-PLG microparticle formulation (Lot 0156-046) along with results of two microparticle formulations containing the TEPHELAST® polymer. One of the TEPHELAST® formulations was prepared with 100% of the TEPHELAST® polymer while the other was prepared using a polymer blend comprising 10% (by weight) of the TEPHELAST® polymer and 90% of the 75:25 DL-PLG polymer.

As observed previously, the microparticle formulation prepared from the standard polyester material (the 75:25 DL-PLG microparticle formulation) was only able to be injected successfully through the 21 G needle at lower concentration levels. However, the nalmefene-loaded microparticle formulations prepared from the TEPHELAST® polymer and from a blend of the TEPHELAST® polymer demonstrated injectability through 23 G needles at all concentration levels tested including the 50% concentration level, a marked improvement over the injectability exhibited by the standard polyester example.

Example 17

Injectability Testing of Blends of Different Microparticle Formulations Using a TEPHELAST® Formulation In this example, portions of a TEPHELAST® microparticle formulation which, on its own, exhibits enhanced injectability properties, was blended with microparticle formulations prepared from standard biodegradable polymers that, on their own, exhibit poor injectability properties. In this example, the TEPHELAST® microparticle formulation consisted of 100% of the TEPHELAST® 30% copolymer. This microparticle formulation was blended into 75:25 DL-PLG and DL-PL microparticle formulations. In both cases, the blends contained only 25% by weight of the TEPHELAST® microparticle material. Blending was conducted by weighing out the indicated amount of each microparticle formulation into the syringe during preparation of the test syringes. The dry microparticle formulations were then evaluated for syringe injectability using the 0.1 wt % TWEEN® 80 injection vehicle.

Listed in Table 24 are the injectability data of the unblended microparticle formulations prepared from the DL-PL and the 75:25 DL-PLG polymers. Alongside each of these columns are the results for the blends of these microparticle formulations with 25% by weight of the TEPHELAST® microparticle formulation.

TABLE 24

Batch information and injectability screening results from Example 17.

| Formulation Parameters Needle size (Gauge) | Susp. Conc. | 75:25 DL-PLG | Blends of microparticle formulations: 75%: 75:25 DL-PLG 25%: TephELAST | DL-PL | Blends of microparticle formulations: 75% DL-PL 25% TephELAST |
|---|---|---|---|---|---|
| Formulation lot Number | | — | — | — | — |
| Microparticle formulation component 1 | | 100% 00156-006 (DL-PLG) | 75% 00156-006 (DL-PLG) | 100% 0037-099 | 75% 0037-099 |
| Microparticle formulation component 2 | | | 25% 0037-029 (TephELAST) | | 25% 0037-029 |
| Dry sieve performed | | Yes (300 micron) | Yes (300 micron) | Yes (300 micron) | Yes (300 micron) |
| Mean particle size, microns | | na | Na | na | na |
| D(90) particle size, microns | | na | Na | na | na |
| 21 G | 10% | | | | |
| | 20% | Pass | Pass | Fail | Pass |
| | 30% | | | | |
| | 40% | | | | |
| | 50% | Pass | Pass | Fail | Pass |
| 23 G | 10% | Fail | | | Fail |
| | 20% | Fail | Pass | Fail | Fail |
| | 30% | | Pass | | |
| | 40% | | | Fail | |
| | 50% | Fail | Pass | Fail | Fail |
| 25 G | 10% | | Fail | Fail | Fail |
| | 20% | | Fail | Fail | |
| | 30% | | | | |
| | 40% | | | | |
| | 50% | | | | |

NOTES:

"na" indicates that particle sizes were not determined on blends of individual microparticle formulations; refer to particle size results from individual batches used to prepare these blends.

It has been found that blending a small proportion of a microparticle composition that possesses good injectability properties can improve the injectability of another microparticle composition. Blending allowed the 75:25 DL-PLG microparticle composition to be successfully delivered through a 23 G needle at all concentration levels tested. Similarly, blending allowed the DL-PL microparticle composition to be successfully delivered through a 21 G needle at all concentration levels tested. These results are marked improvements over the injectability of the un-blended microparticle compositions.

Example 18

Effects of Terminal Sterilization Treatment

A portion of the high molecular weight TEPHELAST® 30% microparticle composition from Example 12 (Lot 0037-029; Table 19) was treated to 2.5 Mrad gamma-irradiation as a means of terminal sterilization. Irradiation was performed by Neutron Products (Dickerson, Md.) on samples that were frozen on dry ice prior to and during the irradiation operation. Dosimeters included in the actual irradiation container indicated that samples were exposed to an actual dose in the range of about 2.53-2.66 Mrad.

The dry microparticle formulation was evaluated for syringe injectability using the 0.1 wt % TWEEN® 80 injection vehicle. The sample was tested for injectability as it was received following the gamma-irradiation process; without additional sieving.

Results of injectability testing are presented in Table 25 and demonstrate that the improved injectability properties of these compositions are retained after treatment to the gamma-irradiation process. For reference, the injectability screening results of the non-irradiated microparticles are presented in Table 20.

TABLE 25

Batch information and injectability screening results of Example 18.

| Formulation Parameters Needle size (Gauge) | Suspension conc., wt % | TephELAST 30% (high MW) |
|---|---|---|
| Lot Number | | 0037-029 |
| Component 1 | | 100% F |
| Component 2 | | |
| Component 3 | | |
| Terminal Sterilization treatment? | | Yes - 2.5Mrad |
| 21 G | 10% | |
| | 20% | |
| | 30% | |
| | 40% | |
| | 50% | Pass |
| 23 G | 10% | |
| | 20% | |
| | 30% | |
| | 40% | |
| | 50% | Pass |
| 25 G | 10% | |
| | 20% | Pass |
| | 30% | |
| | 40% | |
| | 50% | Pass |

Example 19

Capillary Viscometry Testing of Concentrated Suspensions of TEPHELAST® Microparticle Formulations Suspended in Injection Vehicle Media In order to characterize the flow characteristics of concentrated microparticle suspensions through small-diameter orifices, capillary viscometry was utilized in order to compare the flow properties of various microparticle formulations.

Microparticle formulations were suspended in the same 0.1 wt % TWEEN® 80 injection vehicle used throughout these investigations. Capillary fall times were measured on concentrated suspensions containing 40% solids (by weight) of the microparticle suspension in the injection vehicle. Capillary viscometry testing was carried out on the injection vehicle itself and on suspensions of microparticle formulations that did not exhibit any improved injectability effects. These samples include a microparticle composition prepared with the 75:25 DL-PLG and another prepared using the TEPHAFLEX® polymer. Testing was also carried out on two microparticle compositions prepared with the TEPHELAST® polymer that earlier were shown to exhibit the improved injectability effect. The results are shown in Table 26.

TABLE 26

Fall time measurements, by capillary viscometry, of injection vehicle and 40% microparticle suspensions in the injection vehicle from Example 19. Measurements conducted at 22° C. using a Canon-Fenske #150 capillary viscometer. Injection vehicle: TWEEN ® 80.

| Sample description | Microparticle formulation lot number | Fall time, seconds (mean ± sd) |
|---|---|---|
| Injection vehicle only | — | 34 ± 1 |
| 75:25 DL-PLG microparticle formulation | 00061-020 | 400 ± 3 |
| TephaFLEX ®, low molecular weight | 00037-023 | 399 ± 2 |
| TephELAST, high molecular weight, 30% copolymer ratio | 00037-029 | 351 ± 2 |
| Microparticle formulation prepared from a 90:10 blend of 75:25 DL-PLG:TephELAST | 00061-137 | 355 ± 6 |

As shown in Table 26, the DL-PLG and the TEPHAFLEX® samples had fall times of 400 seconds. In contrast, the fall times of the two TEPHELAST® formulations were appreciably faster (350-355 seconds). In this case, as was shown earlier in other examples, microparticle compositions that exhibit faster flow through the small-diameter tubes of the capillary viscometers are the same formulations that demonstrate the improved injectability effect.

Example 20

Injectability Results of Surfactant and Non-Surfactant Compositions

Compositions were prepared to show successful injectability of the polymers of this invention without the use of a surfactant. Microparticle formulations and conventional formulations utilizing deionized water without a surfactant versus utilizing 0.5% CMC viscosity modifying agent and 0.1% TWEEN® 80 surfactant in water were compared. The results are shown in Table 27.

TABLE 27

Injectability results of surfactant and non-surfactant compositions from Example 20.

| Needle Size | Formulation Parameters | Suspension Conc. | 75:25 DL-PLG | 75:25 DL-PLG | DL-PL PCL | DL-PL PCL |
|---|---|---|---|---|---|---|
| | Lot Number | | 00156-018 | 00156-018 | 00156-090 | 00156-090 |
| | Excipient solvent | | Ethyl Acetate | Ethyl Acetate | Methylene Chloride | Methylene Chloride |
| | Component 1 | | 100% A | 100% A | 95% V | 95% V |
| | Component 2 | | | | 5% C | 5% C |
| | Component 3 | | | | | |
| | Sieve conditions | | Yes 300 micron | Yes 212 micron | Yes 300 micron | Yes 300 micron |
| | Particle size 90% (D90) | | 100.8 | 110.8 | 114.4 | 114.4 |

TABLE 27-continued

Injectability results of surfactant and non-surfactant compositions from Example 20.

| Needle Size | Formulation Parameters | Suspension Conc. | 75:25 DL-PLG | 75:25 DL-PLG | DL-PL PCL | DL-PL PCL |
|---|---|---|---|---|---|---|
| | Particle size, mean | | 62.7 | 62.7 | 82.7 | 82.7 |
| | Drug loading | | na | na | na | na |
| | Polymer Concentration wt % | | 20 | 20 | 20 | 20 |
| | Injection vehicle | | D.I. Water | 0.5% CMC 0.1% TWEEN ® 80 | D.I. Water | 0.5% CMC 0.1% TWEEN ® 80 |
| 21-G | | 10% | | | | |
| | | 20% | Pass | Pass | Pass | Pass |
| | | 30% | | | | |
| | | 40% | | | | |
| | | 50% | | Fail | | Pass |
| 23-G | | 10% | | | | |
| | | 20% | Fail | Fail | Pass | Pass |
| | | 30% | | | | |
| | | 40% | | Fail | | |
| | | 50% | Fail | Fail | Pass | Pass |
| 25-G | | 10% | | Fail | | |
| | | 20% | Fail | | Pass | Pass |
| | | 30% | | | | Pass |
| | | 40% | | | | Fail |
| | | 50% | | | Fail | Fail |

The results of the injectability screening of these microparticle compositions in Table 27 show that the compositions can be utilized for a larger particle size than a conventional microparticle and yet pass the syringe screening at a much smaller needle size even where the compositions do not contain a surfactant (compare DL-PL+PCL in D.I. water with 75:25 DL-PLG in 0.5% CMC+0.1% TWEEN® 80). Thus, the compositions even without a surfactant are still effective, and in fact superior over conventional compositions.

Example 21

Atomic Force Microscopy (AFM) Measurements of Microparticle Surfaces

Nanoparticles prepared from blends of polylactide and polycaprolactone (e.g., 95:5, 90:10, and 50:50 blends of polylactide and polycaprolactone) and polylactide/polycaprolactone/polylactide-co-glycolide blends (e.g., 90% 75:25 PLG, 7.5% PL, and 2.5% PCL) were characterized by atomic force microscopy (AFM). Microparticles prepared from these blends exhibited nanotexturing or dimpling on the surface of the particles. This nanotexturing is not observed in microparticles prepared from homogeneous polymer blends. Thus, it is hypothesized that such dimpling occurs as a result of immiscible polymer blends which phase separate into identifiable domains.

Atomic force microscopy was performed using a Digital Instruments Dimension 3100 instrument in order to compare and contrast the surface characteristics of individual microparticles from various formulations. Atomic force microscopy (AFM) uses a nanometer size silicon tip that is placed in contact on the surface of a sample to scan back and forth, mapping out changes in sample topography and roughness. The AFM can image regions as large as 100 μm, or down to 1 μm with nanometer resolution using minute surface forces to limit interaction and potential damage to a sample. In phase-contrast mode, the silicon tip is oscillated at high frequency to "tap" across a given surface. The oscillation output of the tip is measured and compared to the driving oscillation force, and any differences are mapped out to show changes in the sample stiffness or hardness.

In the following experiments, the "tapping mode" was applied whereby the tip oscillated at around 300 kHz as it scanned across the surface. The tapping mode allowed measurement of both topography and "phase shift". The phase shift is a measure of the energy dissipated by the tip as it presses into the surface. If properly configured, regions of low phase shift (dark color in an image) correspond to soft materials, and regions of high phase shift (bright color in the image) correspond to hard materials.

In the case of the present microparticle formulations, the sample was immobilized on a glass slide and the AFM tip was placed directly on the top of an individual microparticle. Topography and phase-contrast images were then collected over 5 μm square regions across the surface of an individual microparticle in order to look for differences in roughness, as well as changes in surface stiffness. Microparticles composed of two or more miscible (homogeneous) components will show homogeneous monotone phase-contrast images with little contrast or variation across the surface. In contrast, microparticles with immiscible (heterogeneous) components will show some contrast or variation in the phase-contrast images, representing the individual components across the surface of the microparticle.

Control

AFM images of a 5 micron×5 micron surface of a control microparticle composed of poly(DL-lactide) (microparticle lot 0156-135-00) were obtained. The surface of a microparticle from this control formulation exhibited a homogeneous, featureless surface (i.e., smooth, homogeneous polymer surfaces) in both the topography and phase-contrast modes consistent with a completely miscible, homogeneous polymer matrix.

95:5 blend of poly(DL-lactide) and polycaprolactone, Lot 0156-137-00

AFM images of a 5 micron×5 micron surface of a microparticle composed of a 95:5 blend of poly(DL-lactide) and polycaprolactone (microparticle lot 0156-137-00) were obtained. The surface of the microparticles exhibited nanotexturing or dimpling on both the topography and phase-contrast mode.

Various modifications and variations can be made to the compositions, articles, devices, and methods described herein. Other aspects of the compositions, articles, devices, and methods described herein will be apparent from consideration of the specification and practice of the compositions, articles, devices, and methods disclosed herein.

Example 22

Admixtures of DL-PL and PCL with Additional PLG Polymers

Microparticles can be prepared from admixtures of DL-PL and PCL with other biocompatible, optionally biodegradable polymers. Microparticle compositions were prepared as follows. Admixtures consisting of either 75:25 or 90:10 (by weight) of DL-PL and PCL, respectively, were prepared. The DL-PL/PCL mixtures were blended, as indicated, with a 65:35 poly(DL-lactide-co-glycolide) (PLO) copolymer for preparation of microparticles. Compositions were prepared using 20%, 40%, or 60% by weight of the PL/PCL admixture with the remainder of the polymer composition containing the 65:35 PLG. Microparticle compositions were prepared using methylene chloride and a DP polymer solution concentration of 20%. Four compositions were prepared from blends of the PL and PCL admixture with the 65:35 PLG. The final compositions of these formulations and the results of their injectability testing are shown in Table 28. Table 28 is shown below after Example 23.

The injectability results of formulation 00300-050 demonstrate that 90:10 ratios of DL-PL and PCL can be useful in improving injectability of microparticle compositions. In this case, 40% of the PL/PCL admixture was combined with 60% of a 65:35 PLG thereby making a composition containing 60% 65:35 PLG, 36% DL-PL, and only 4% PCL. In this example, injectability was demonstrated from a 20% suspension through a 25 G needle.

Three formulations were prepared using a 75:25 mixture of DL-PL and PCL. Lots 00300-040, 00300-043, and 00300-046 were prepared using 20%, 40%, and 60% of the PL/PCL admixture, respectively. Improved injectability through 23-G needles was observed from all three formulations. In two cases, injectability through 25-G needles was obtained from suspension concentrations reaching upwards of 50% solids (in the case of lot 00300-040).

Example 23

Effect of Particle Size Distribution on Injectability

The effect of particle size distribution on injectability was evaluated for 5 different microparticle formulations prepared from a 95:5 blend of polylactide and polycaprolactone and having different particle size distributions. The microparticles were injected through a 21 gauge needle at suspension concentrations of 20%, 40%, and 50%. The control was microparticles prepared from poly(DL-lactide). The results of the injectability experiments are provided in Table 29.

TABLE 29

Injectability test results

| | | Injectability results[1] | |
|---|---|---|---|
| Needle Size | Suspension Concentration | Control Sample - poly(DL-lactide) microparticles | Test Samples - 95:5 blend of PL and PCL (5 samples) |
| 21 G | 10% | | |
| | 20% | Fail | Pass |
| | 30% | | |
| | 40% | Fail | Pass |
| | 50% | Fail | Pass |

Figure 1B:
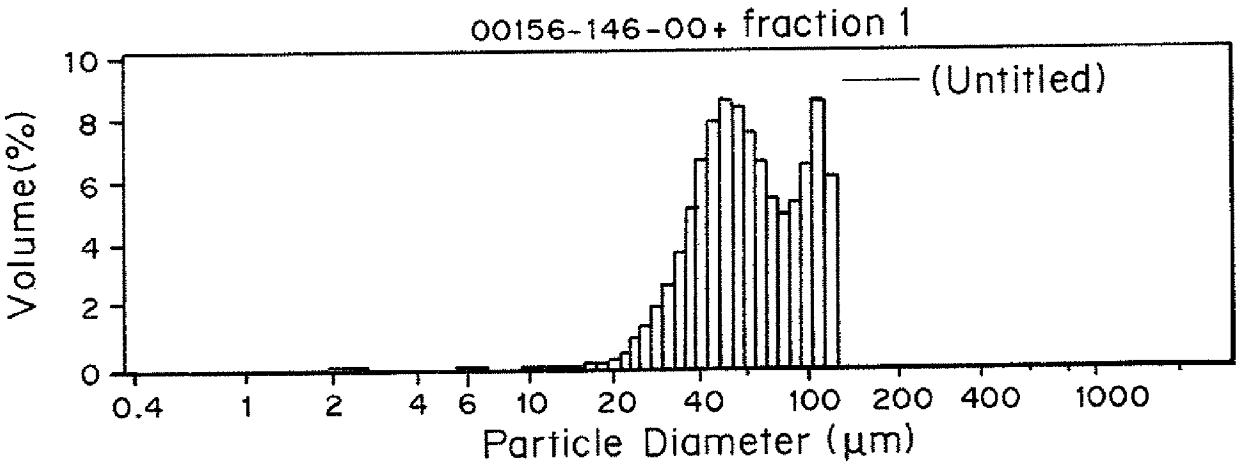
Figure 1C:
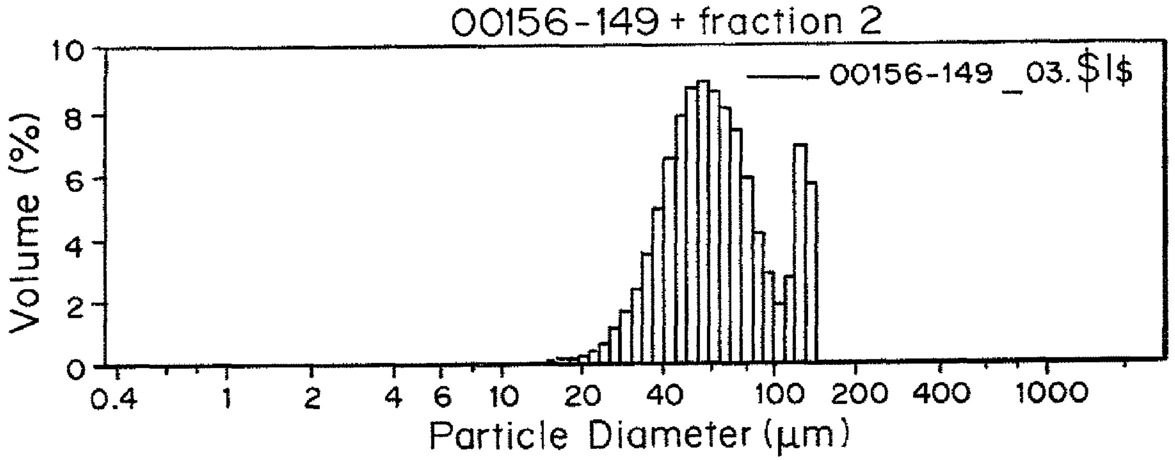
Figure 1D:
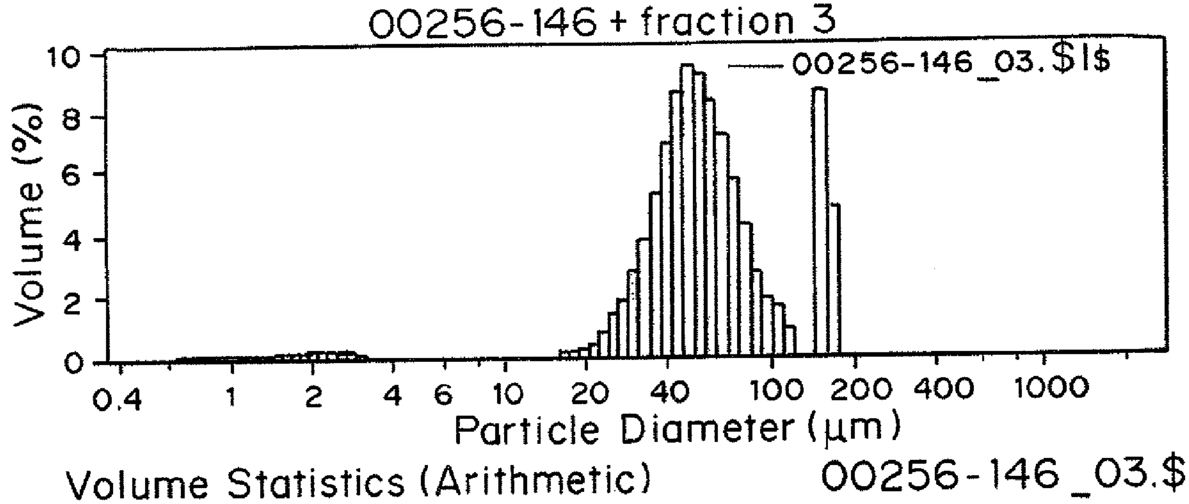
Figure 1E:
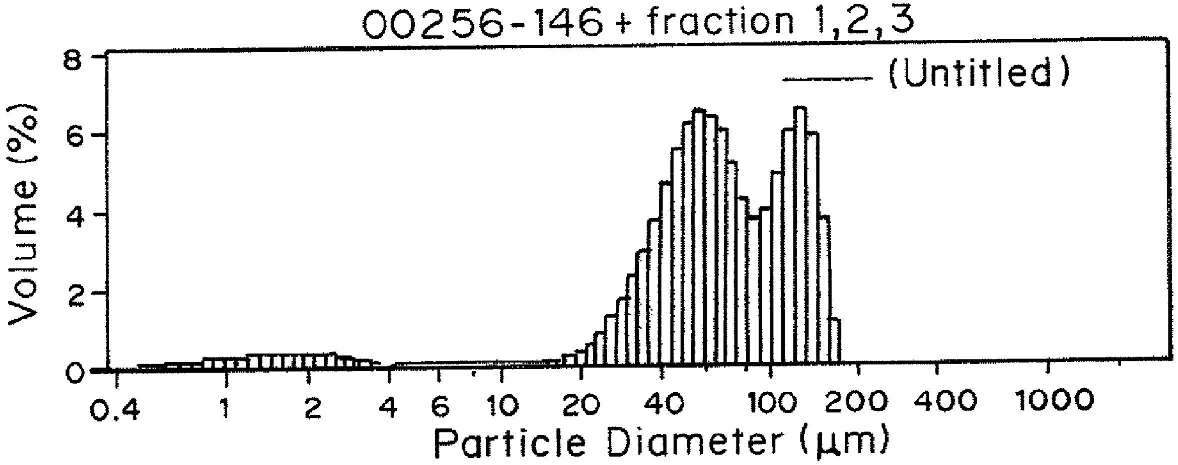

The particle size distribution for the five test samples (Test Samples 1-5) is shown in FIGS. 1A-E.

The results above show that improved injectability is obtained for microparticles obtained from a 95:5 blend of polylactide and polycaprolactone having a range of size distributions versus the poly(DL-lactide) control.

TABLE 28

Batch information and injectability screening results of Example 21.

| Needle Size | Formulation Parameters | Suspension Conc. | 65:35 DL-PLG DL-PL, PCL | 65:35 DL-PLG DL-PL, PCL | 65:35 DL-PLG DL-PL, PCL | 65:35 DL-PLG DL-PL, PCL |
|---|---|---|---|---|---|---|
| | Lot Number | | 00300-50-00 | 00300-040-00 | 00300-43-00 | 00300-046-00 |
| | Excipient solvent | | Methylene Chloride | Methylene Chloride | Methylene Chloride | Methylene Chloride |
| | Component 1 | | 60% D | 80% D | 60% D | 40% D |
| | Component 2 | | 36% B | 15% B | 30% B | 45% B |
| | Component 3 | | 4% C | 5% C | 10% C | 15% C |
| | Sieve conditions | | 300 micron | 300 micron | 300 micron | 300 micron |
| | Particle size 90% | | 111 | 100 | 107 | 109 |
| | Particle size, mean | | 83 | 78 | 77 | 84 |
| | Drug loading | | | | | |
| | Polymer Concentration wt % | | 20 | 20 | 20 | 20 |
| | Formulation Series | | | | | |
| 21-G | | 10% | | | | |
| | | 20% | | | | |
| | | 30% | | | | |
| | | 40% | | | | |
| | | 50% | Pass | Pass | Pass | Pass |

TABLE 28-continued

| | | | | | |
|---|---|---|---|---|---|
| 23-G | 10% | | | | |
| | 20% | Pass | Pass | Pass | Pass |
| | 30% | | | | |
| | 40% | | | | Fail |
| | 50% | Pass | Pass | Pass | Fail |
| 25-G | 10% | | | | |
| | 20% | Pass | Pass | Pass | Fail |
| | 30% | | | | |
| | 40% | | | | |
| | 50% | Fail | Pass | Fail | |

Key to polymers.

| | | |
|---|---|---|
| A | 75:25 DL PLG, IV 0.44 dL/g | Medisorb Lot 7197-339 |
| B | DL-lactide, IV 0.46 dL/g | Lakeshore Lot LP-155 0.46 |
| C | Polycaprolactone (MW 65,000 Da) | Aldrich 01222JD, 65K |
| D | 65:35 DL-PLG, COOH, IV 0.39 dL/g | BI, Lot RES-0336 |

We claim:

1. An injectable microparticle composition in a kit, the kit comprising a population of microparticles, comprising: (1) a blend of immiscible polymers, (2) a blend of polymers which phase separate into identifiable domains, (3) a copolymer comprising segments which are immiscible, (4) a copolymer comprising segments which phase separate into identifiable domains, or (5) blends thereof, the polymers or copolymers containing monomers selected from the group consisting of glycolide, lactide, caprolactone, and 4-hydroxybutyrate, wherein at least one polymer or blend of polymers is selected from the group consisting of (1) a blend of poly(L-lactide) (L-PL) or poly(DL-lactide) (DL-PL) and polycaprolactone; (2) a copolymer of DL-lactide or L-lactide and caprolactone; (3) a copolymer of DL-lactide or L-lactide, glycolide, and caprolactone; and (4) a blend of L-PL or DL-PL and poly(caprolactone) admixed with poly(lactide-co-glycolide) (PLG), and a liquid vehicle for suspension of the microparticles to produce a solids content of between 10 wt % and less than 100 wt %, wherein the microparticles are injectable when suspended in a vehicle consisting of water, 0.5 wt % sodium carboxymethylcellulose, USP low viscosity grade, and 0.1 wt % polysorbate 80 and a means for injection of the suspension of the microparticles comprising a needle or other device with a lumen, the needle or device having an inner and an outer diameter, wherein (a) the ratio of the needle inner diameter to the mean particle size of the population of microparticles is from 2.0 to 4.5 when the vehicle added to the microparticles forms a suspension with a solids content from 10 wt. % to <30 wt. % or (b) the ratio of the needle inner diameter to the mean particle size of the population of microparticles is from 4.0 to 8.0 when the vehicle added to the microparticles forms a suspension with a solids content ≥30 wt. %.

2. The kit of claim 1, wherein (a) the ratio of the needle inner diameter to the mean particle size is from 3.0 to 4.2 and the solids content is from 10 wt. % to <30 wt. % or (b) the ratio of the needle inner diameter to the mean particle size is from 4.0 to 7.6 and the microparticle concentration is ≥30 wt. %.

3. The kit of claim 1, wherein (a) the ratio of the needle inner diameter to the mean particle size is from 3.0 to 3.8 and the solids content is from 10 wt. % to <30 wt. % or (b) the ratio of the needle inner diameter to the mean particle size is from 4.0 to 4.8 and the solids content is ≥30 wt. %.

4. The kit of claim 1, wherein the solids content is selected from the ranges consisting of from 30 to 60 wt. %, from 30 to 50 wt. %, and from 30 to 45 wt. %.

5. The kit of claim 1 wherein the microparticles comprise a blend of any one or more of the polymers.

6. The kit of claim 5, wherein the blend further comprises one or more of 50/50 PLG, 65/35 PLG, 75/25 PLG, 85/15 PLG, 95/5 PLG, DL-PL, or L-PL.

7. The kit of claim 6, wherein the microparticles comprises a blend of DL-PL and poly(caprolactone) and one or more of 50/50 PLG, 65/35 PLG, 75/25 PLG, 85/15 PLG, 95/5 PLG, DL-PL, or L-PL.

8. The kit of claim 6, wherein the PLG is 65/35 PLG, and the concentration of the L-PL and polycaprolactone blend in the mixture is between about 20% and about 40% by weight.

9. The kit of claim 1, wherein the microparticles comprise a blend of DL-PL and poly(caprolactone), wherein the blend is more than 0 wt. % and up to 30 wt. % polycaprolactone and from 70 wt. % to less than 100 wt. % DL- or L-lactide.

10. The kit of claim 1, wherein the microparticles comprise a copolymer of DL-lactide, glycolide, and caprolactone.

11. The kit of claim 1, wherein the microparticles comprise poly(4-hydroxybutyrate-co-3-hydroxybutyrate), or a blend thereof.

12. The kit of claim 1 wherein the needle is a 23 gauge needle or smaller inner diameter needle.

13. The kit of claim 1 wherein the means for injection is selected from the group consisting of a hypodermic needle, a tube, and a catheter.

14. The kit of claim 1 wherein the microparticle composition further comprises a prophylactic, diagnostic or therapeutic agent.

15. The kit of claim 1, wherein the ratio of D90/D10 for the microparticles is from about 2 to about 10.

16. The kit of claim 15, wherein the ratio of D90/D10 for the microparticles is from about 2 to about 8.

17. The kit of claim 15, wherein the ratio of D90/D10 for the microparticles is from about 2 to about 5.

18. A method for delivering a microparticle composition to a subject comprising administering through a needle or other device including a lumen having an inner diameter, a population of microparticles suspended in a liquid vehicle, wherein (a) the ratio of the needle inner diameter to the mean particle size of the population of microparticles is from 2.0 to 4.5 when the vehicle added to the microparticles forms a suspension with a solids content from 10 wt. % to <30 wt. % or (b) the ratio of the needle inner diameter to the mean particle size is from 4.0 to 8.0 when the vehicle added to the microparticles forms a suspension with a solids content ≥30 wt. %, wherein the microparticles comprise (1) a blend of immiscible polymers, (2) a blend of polymers which phase separate into identifiable domains, (3) a copolymer comprising segments which are immiscible, (4) a copolymer comprising segments which phase separate into identifiable domains, or (5) blends thereof, the polymers or copolymers containing monomers selected from the group consisting of glycolide, lactide, caprolactone, and 4-hydroxybutyrate, wherein at least one polymer or blend of polymers is selected from the group consisting of (1) a blend of L-PL or DL-PL and polycaprolactone; (2) a copolymer of DL-lactide or L-lactide and caprolactone; (3) a copolymer of DL-lactide or L-lactide, glycolide, and caprolactone; and (4) a blend of L-PL or DL-PL and poly(caprolactone) admixed with PLG; and wherein the microparticles are injectable when suspended in a vehicle consisting of water, 0.5 wt % sodium carboxymethylcellulose, USP low viscosity grade, and 0.1 wt % polysorbate 80.

19. The method of claim 18, wherein the needle is a 23 gauge needle or smaller inner diameter needle.

20. The method claim 18, wherein the mean particle size is less than 110 microns.

21. The method of claim 18, wherein (a) the ratio of the needle inner diameter to the mean particle size is from 3.0 to 4.2 and the microparticle concentration is from 10 wt. % to <30 wt. % or (b) the ratio of the needle inner diameter to the mean particle size is from 4.0 to 5.7 and the microparticle concentration is ≥30 wt. %.

22. The method of claim 21, wherein the microparticle concentration is from 30 to 60 wt. %, from 30 to 50 wt. %, or from 30 to 45 wt. %.

23. The method of claim 18, wherein (a) the ratio of the needle inner diameter to the mean particle size is from 3.0 to 3.8 and the microparticle concentration is from 10 wt. % to <30 wt. % or (b) the ratio of the needle inner diameter to the mean particle size is from 4.0 to 4.8 and the microparticle concentration is ≥30 wt. %.

24. The method of claim 18, wherein the microparticles comprise poly(4-hydroxybutyrate-co-3-hydroxybutyrate).

25. The method of claim 18, wherein the microparticles comprise a blend of any one or more of the polymers.

26. The method of claim 25, wherein the blend further comprises one or more of 50/50 PLG, 65/35 PLG, 75/25 PLG, 85/15 PLG, 95/5 PLG, DL-PL, or L-PL.

27. The method of claim 26, wherein the microparticles comprises a blend of DL-PL and poly(caprolactone) and one or more of 50/50 PLG, 65/35 PLG, 75/25 PLG, 85/15 PLG, 95/5 PLG, DL-PL, or L-PL.

28. The method of claim 27, wherein the PLG is 65/35 PLG, and the concentration of the L-PL and polycaprolactone blend in the mixture is between about 20% and about 40% by weight.

29. The method of claim 18, wherein the microparticles comprise a blend of DL-PL or L-lactide and poly(caprolactone), wherein the blend is more than 0 wt. % and up to 30 wt. % polycaprolactone and from 70 wt. % to less than 100 wt. % DL- or L-lactide.

30. The method of claim 18 wherein the microparticles comprise a copolymer of DL-lactide, glycolide, and caprolactone.

31. The method of any of claim 25, 29, 26, 27, or 28, wherein the microparticles are dimpled or comprise nanotexture on the surface.

32. The method of claim 18, wherein the microparticles comprise poly(4-hydroxybutyrate-co-3-hydroxybutyrate), or a blend thereof.

33. The method of claim 18, wherein the liquid carrier comprises water.

34. The method of claim 33, wherein the liquid carrier further comprises a surfactant.

35. The method of claim 18, wherein the microparticles further comprise an active agent.

36. The method of claim 18, wherein the ratio of D90/D10 for the microparticles is from about 2 to about 10.

37. The method of claim 36, wherein the ratio of D90/D10 for the microparticles is from about 2 to about 8.

38. The method of claim 36, wherein the ratio of D90/D10 for the microparticles is from about 2 to about 5.

* * * * *